United States Patent
Von Hollen et al.

(10) Patent No.: US 9,555,202 B2
(45) Date of Patent: Jan. 31, 2017

(54) RESPIRATORY DRUG DELIVERY APPARATUS WHICH PROVIDES AUDIO INSTRUCTIONS

(75) Inventors: Dirk Von Hollen, Clark, NJ (US); Robert Koshinskie, Cranford, NJ (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 431 days.

(21) Appl. No.: 13/060,319

(22) PCT Filed: Aug. 15, 2009

(86) PCT No.: PCT/IB2009/053604
§ 371 (c)(1),
(2), (4) Date: May 16, 2011

(87) PCT Pub. No.: WO2010/023591
PCT Pub. Date: Mar. 4, 2010

(65) Prior Publication Data
US 2011/0226242 A1  Sep. 22, 2011

Related U.S. Application Data

(60) Provisional application No. 61/091,546, filed on Aug. 25, 2008.

(51) Int. Cl.
*A61M 15/00* (2006.01)
*A61M 16/00* (2006.01)

(52) U.S. Cl.
CPC ....... *A61M 15/009* (2013.01); *A61M 15/0013* (2014.02); *A61M 15/0023* (2014.02);
(Continued)

(58) Field of Classification Search
CPC ..... A61B 5/08; A61M 11/00; A61M 15/0013; A61M 15/0016; A61M 15/0026; A61M 15/0065; A61M 15/0083; A61M 15/0091
(Continued)

(56) References Cited

U.S. PATENT DOCUMENTS 4,470,412 A   9/1984   Nowacki et al.
4,484,577 A * 11/1984  Sackner et al. .......... 128/203.28
(Continued)

FOREIGN PATENT DOCUMENTS

EP    0667168 A1   8/1995
EP    1407794 A1   4/2004
(Continued)

OTHER PUBLICATIONS

M. Lee et al; "Results of a Programme to Improve House Staff US of Metered Dose Inhallers and Spacers", Post Graduate Medical Journal, vol. 79, pp. 221-225, 2003.
(Continued)

*Primary Examiner* — Justine Yu
*Assistant Examiner* — Timothy Stanis
(74) *Attorney, Agent, or Firm* — Michael W. Haas

(57) ABSTRACT

A respiratory drug delivery apparatus that includes a housing for holding a source of a medication, wherein the housing has a patient interface portion for delivering one or more doses of the medication to an airway of a patient, and a sound generator coupled to the housing. The sound generator is adapted to generate one or more audible instructions in response to an actuation signal. The actuation signal may generated in response to a manual actuation performed by the patient, or in response to the detection of an event relating to operation of the apparatus.

63 Claims, 19 Drawing Sheets

(52) U.S. Cl.
CPC . *A61M 15/0086* (2013.01); *A61M 2016/0027* (2013.01); *A61M 2016/0039* (2013.01); *A61M 2202/064* (2013.01); *A61M 2205/183* (2013.01); *A61M 2205/43* (2013.01); *A61M 2205/44* (2013.01); *A61M 2205/581* (2013.01); *A61M 2205/8206* (2013.01)

(58) Field of Classification Search
USPC .......... 128/200.14, 200.23, 202.22, 202.27,128/203.15, 205.23, 905
See application file for complete search history.

(56) References Cited

U.S. PATENT DOCUMENTS

| | | | |
|---|---|---|---|
| 4,809,692 A | | 3/1989 | Nowacki et al. |
| 4,832,015 A | | 5/1989 | Nowacki et al. |
| 4,898,060 A | * | 2/1990 | To .................................. 84/95.2 |
| 4,984,158 A | | 1/1991 | Hillsman |
| 5,012,803 A | | 5/1991 | Foley et al. |
| 5,042,467 A | | 8/1991 | Foley |
| 5,331,953 A | * | 7/1994 | Andersson et al. ..... 128/200.14 |
| 5,363,842 A | * | 11/1994 | Mishelevich et al. ... 128/200.14 |
| 5,385,140 A | | 1/1995 | Smith |
| 5,809,997 A | * | 9/1998 | Wolf ....................... 128/200.23 |
| 5,848,599 A | | 12/1998 | Todd |
| 5,905,618 A | * | 5/1999 | Cases et al. .................... 361/88 |
| 6,190,326 B1 | * | 2/2001 | McKinnon et al. .......... 600/529 |
| 6,202,642 B1 | * | 3/2001 | McKinnon et al. ..... 128/200.23 |
| 6,358,058 B1 | * | 3/2002 | Strupat et al. ................ 434/262 |
| 6,359,987 B1 | * | 3/2002 | Tran et al. ...................... 381/58 |
| 6,557,549 B2 | | 5/2003 | Schnidt et al. |
| 2002/0026935 A1 | | 3/2002 | Schmidt et al. |
| 2002/0121275 A1 | | 9/2002 | Johnson et al. |
| 2002/0148462 A1 | * | 10/2002 | Fugelsang ......... A61M 15/0086 128/200.14 |
| 2005/0022806 A1 | * | 2/2005 | Beaumont et al. ...... 128/200.14 |
| 2005/0150897 A1 | * | 7/2005 | Fabricius et al. ................. 221/2 |
| 2005/0174216 A1 | | 8/2005 | Lintell |
| 2005/0247305 A1 | * | 11/2005 | Zierenberg et al. ..... 128/200.14 |
| 2006/0130838 A1 | * | 6/2006 | Lee et al. ................. 128/205.23 |
| 2006/0243277 A1 | | 11/2006 | Denyer et al. |
| 2007/0062519 A1 | * | 3/2007 | Wuttke et al. ........... 128/200.14 |
| 2007/0076067 A1 | | 4/2007 | Hamano |
| 2007/0129708 A1 | * | 6/2007 | Edwards et al. ........... 604/890.1 |

FOREIGN PATENT DOCUMENTS

| | | |
|---|---|---|
| JP | 2002540857 A | 12/2002 |
| JP | 2005523773 A | 8/2005 |
| JP | 2007097787 A | 4/2007 |
| WO | 2008091838 A2 | 7/2008 |

OTHER PUBLICATIONS

Laura T. Scarpaci et al; "Assessment of Hospice Nurses' Technique in the Use of Inhalers and Nebulizers", Palliative Medicine, vol. 10, No. 2, 2007.

James B. Fink et al; "Problem With Inhaler Use: A Call for Improved Clinician and Patient Education", Respiratory Care, vol. 50, No. 10, Sep. 2005.

* cited by examiner

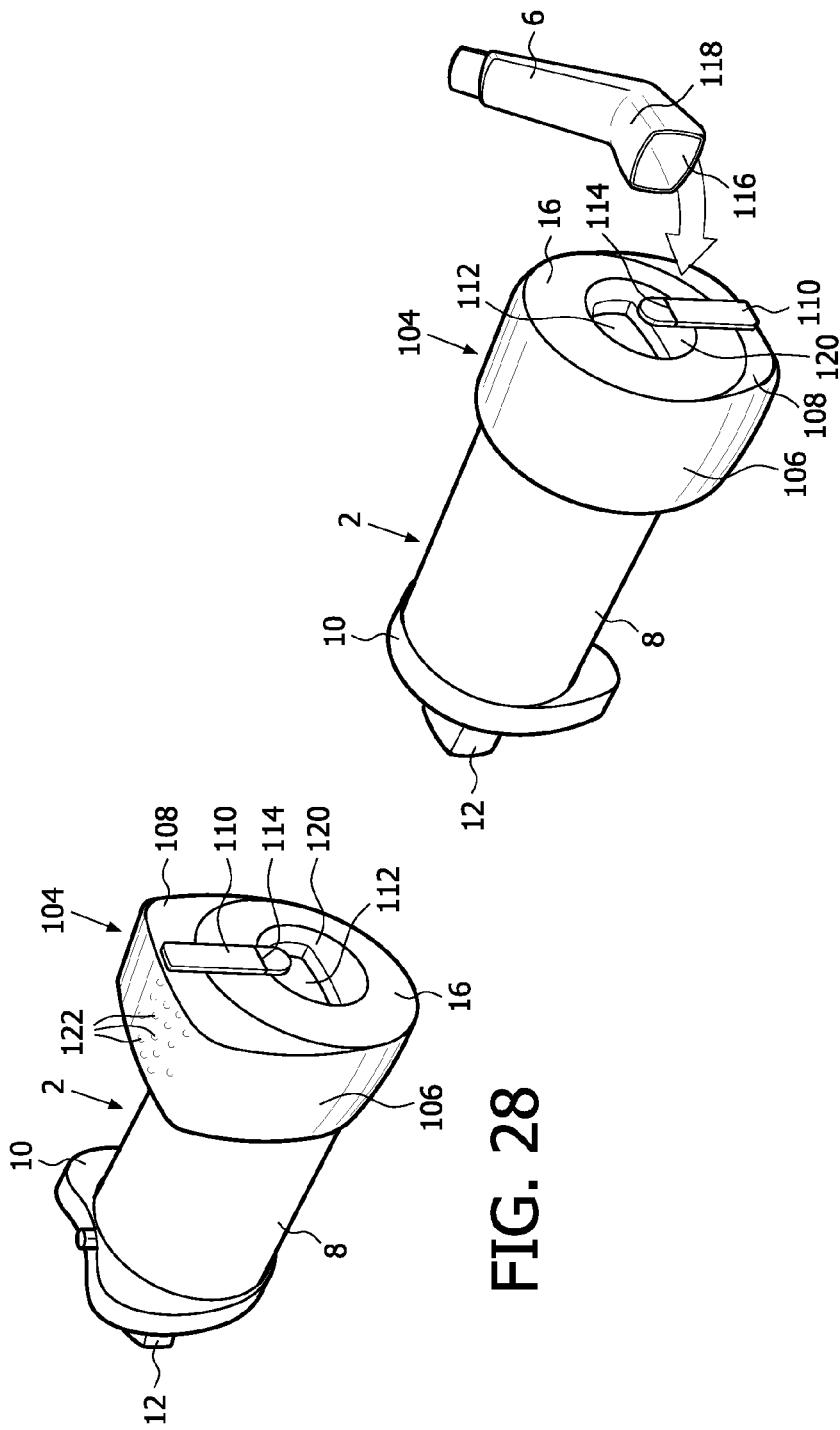

RESPIRATORY DRUG DELIVERY APPARATUS WHICH PROVIDES AUDIO INSTRUCTIONS

This patent application claims the priority benefit under 35 U.S.C. §119(e) of U.S. Provisional Application No. 61/091,546 filed on Aug. 25, 2008, the contents of which are herein incorporated by reference.

The present invention pertains to an apparatus for delivering a respiratory drug to a patient, such as, without limitation, a metered dose inhaler (MDI), a valved holding chamber for use with an MDI, a dry powder inhaler (DPI) or a nebulizer, and, in particular, to a respiratory drug delivery apparatus which provides audio instructions to a patient, particularly in situations where the patient is required to regularly self medicate using the respiratory drug delivery apparatus.

It is well known to deliver a medication to a patient's respiratory system to treat a medical condition using a respiratory drug delivery apparatus. For example, a patient suffering from an acute asthmatic attack may use a respiratory drug delivery apparatus to deliver a bronchodilator, such as albuterol (salbutamol), in the form of a fine mist to the patient's respiratory system.

One known respiratory drug delivery apparatus consists of a metered dose inhaler (MDI) and a spacer. The MDI, also known simply as an "inhaler", includes a canister or nebulizer that contains the medication under pressure and a canister holder, which is typically "L" shaped. Although it is common for a patient to use the canister holder as a mouthpiece for receiving the aerosolized medication into their airway directly from the aerosol dispensing leg of the canister holder, this configuration may not optimize the mixing of the medication with the air because the aerosolized medication is injected directly into the airway. Without adequate mixing of the drug with the air, the medication may not be inhaled into the patient's lungs where it is effective, but may form as droplets that are deposited in the patient's mouth and swallowed without the desired medicinal effect.

To enhance mixing of the medication with air, it is known to provide a spacer, also commonly referred to as a valved holding chamber, that attaches to the aerosol dispending end of the canister holder. The spacer, which is typically a small hollow cylinder with a one-way valve at the downstream end, receives the aerosol from the canister and allows it to form into a fine mist for inhalation into the airway of the patient. Optionally, a mask may be provided at the end of the spacer opposite the MDI so that the patient can breath through his or her mouth to receive the medication. Examples of conventional spacers and associated components are shown in U.S. Pat. Nos. 4,470,412; 4,809,692; and 4,832,015 all to Nowacki et al.; U.S. Pat. No. 5,012,803 to Foley et al.; U.S. Pat. No. 5,042,467 to Foley; U.S. Pat. No. 5,385,140 to Smith, U.S. Pat. No. 5,848,599 to Foley et al., and U.S. Pat. No. 6,557,549 to Schmidt et al. Other known respiratory drug delivery apparatuses include dry powder inhalers (DPIs) and nebulizers.

Proper use of a medical device such as a respiratory drug delivery apparatus is essential, particularly in situations where a patient is required to regularly self-medicate to manage their disease condition. This is often the case in respiratory disease situations where the patient is typically provided with a respiratory drug delivery apparatus and is expected to self-manage their respiratory disease condition using the respiratory drug delivery apparatus. Normally, a medical professional will provide the initial education to the patient as to how to use the respiratory drug delivery apparatus in order to self-administer the respiratory medication properly. As will be appreciated, the effectiveness of this method of training is largely based on the knowledge and skill level of the medical professional as well as the amount of time that this professional can spend with the patient, which is often limited.

In the area of respiratory drug delivery, a number of assessments have been conducted to quantify the knowledge level of medical professionals on the proper administration of medication using a respiratory drug delivery apparatus such as an MDI or an MDI with a valved holding chamber. Unfortunately, such assessments have not been encouraging. One particular study involving medical professionals indicated that the percentage of participants that correctly completed the proper steps for use of an MDI alone was 67.6%, the percentage of participants that correctly completed the proper steps for use of an MDI with a spacer was 49.9%, and the percentage of participants that correctly completed the proper steps for use of a nebulizer was 38%. This study was reported in Laura T. Scarpaci, *Pharm. D., "Assessment of Hospice Nurses' Technique in the Use of Inhalers and Nebulizers," Palliative Medicine Vol.* 10, No. 2, 2007. Another study directed to medical professionals in a hospital setting relating to MDI and spacer use showed that only 5% used an MDI perfectly. This improved to 13% after a lecture and demonstration and 73% after intensive one-on-one sessions. This study was reported in M. Lee-Wong, *"Results of a Programme to Improve House Staff Use of Metered Dose Inhalers and Spacers," Post Graduate Medical Journal, Vol.* 79, pages 221-225, 2003.

Another study was conducted in order to quantify the knowledge level of patients on the administration of medication using an MDI alone. The results indicated that 28%-68% of patients do not effectively use their MDI. In addition, a patient's reading level has been correlated to improper techniques in using an MDI. Specifically, poor technique, identified as less than or equal to three correct steps being performed, was found on 89% of patients who read at the third grade level and 48% of patients who read at the high school level. This study was reported in James B. Fink, *"Problem with Inhaler Use: A Call for Improved Clinician and Patient Education," Respiratory Care, Vol.* 50, No. 10, September 2005.

Moreover, medical devices such as respiratory drug delivery apparatuses are typically provided with a set of written instructions. However, such instructions are in many cases never read by the patient and/or not consulted and/or used during use of the device (patients may dispose of the instructions or store the instructions separately from the device itself).

Thus, it is evident that there is a long felt but unresolved need for a respiratory drug delivery apparatus which enhances treatment by encouraging proper use of the apparatus by the patient. This is particularly true in situations which require patients to self-medicate separate from the oversight of a health professional, as is often the case with respiratory disease management.

In one embodiment, the invention provides a respiratory drug delivery apparatus that includes a housing for holding a source of a medication, wherein the housing has a patient interface portion for delivering one or more doses of the medication to an airway of a patient, and a sound generator coupled to the housing. The sound generator is adapted to generate one or more audible instructions in response to an actuation signal. The actuation signal may generated in response to a manual actuation performed by the patient. In such a case, the sound generator is preferably operatively coupled to a manual actuator, and the manual actuation comprises a manual actuation of the manual actuator. The manual actuator may be a button that is pressed by the user. Alternatively, the apparatus may included a cap structured to be removeably attached to a portion of the housing, and the manual actuation may comprise the removal of the cap from the housing. In such an embodiment, the apparatus preferably includes a mechanism, such as a pressure sensor or a switch, for detecting that the cap has been removed from the housing and in response thereto causing the actuation signal to be generated. In still another embodiment, the manual actuation may comprise causing the source of medication to be held by the housing. For example, the source of medication may be adapted to be inserted at least partially within the housing, in which case the causing the source of medication to be held by the housing comprises inserting the source of medication at least partially within the housing. In such an embodiment, the apparatus preferably includes a mechanism, such as a pressure sensor or a switch, for detecting that the source of a medication has been caused to be held by the housing and in response thereto causing the actuation signal to be generated.

The one or more audible instructions may comprises a set of audible instructions, such as pre-recorded instructions that may be in the voice of the user's caregiver, for proper use of the respiratory drug delivery apparatus. In an embodiment where the respiratory drug delivery apparatus is an MDI, the set of audible instructions may include instructions relating to shaking the MDI, actuating the MDI, inhaling, and breath holding. In an embodiment where the respiratory drug delivery apparatus comprises a valved holding chamber for use with an MDI, the set of audible instructions may include instructions relating to shaking the MDI, actuating the MDI, inhaling, and breath holding. In particular, in either embodiment, the set of audible instructions may include an instruction instructing the patient to shake the MDI, an instruction instructing the patient to actuate the MDI, an instruction instructing the patient to inhale slowly, and an instruction instructing the patient to hold his or her breath for a predetermined period of time. Alternatively, the set of audible instructions may include instructions relating to shaking the MDI, actuating the MDI, and taking and counting a certain number of breaths, or instructions relating to shaking the MDI, actuating the MDI, and inhaling for a particular period of time.

In another particular embodiment, the respiratory drug delivery apparatus further includes a sensor for sensing an occurrence of an event relating to the operation of the respiratory drug delivery apparatus. The actuation signal is then generated in response to the occurrence of the event being sensed by the sensor. The one or more audible instructions may, in this embodiment, comprise an instruction relating to a technique for proper use of the respiratory drug delivery apparatus that is related to the event that was sensed by the sensor. The instruction may comprise a command directed to correcting or preventing a negative behavior relating to use of the respiratory drug delivery apparatus, or, alternatively, a command directed to reinforcing a positive behavior relating to use of the respiratory drug delivery apparatus. For example, the event may comprise actuation of the MDI (where the respiratory drug delivery apparatus is the MDI or where the respiratory drug delivery apparatus is a valved holding chamber for holding an MDI). In the case of a valved holding chamber, the event may also comprises an opening of an inhalation valve of the chamber. In either case, the instruction may relate to proper inhalation technique or proper breath hold technique. The event may also comprise a closing of the inhalation valve and the instruction may relate to proper breath hold technique. In still another alternative embodiment, the valved holding chamber may comprise a noisemaker for indicating that a patient is not inhaling properly, and the event may comprise the noisemaker making a sound. In such as case, the instruction preferably relates to proper inhalation technique. Also, the sensor may include a microphone for detecting the sound.

In the preferred embodiment, the sound generator comprises a sound module having a power source and a speaker, and the sound module requires no more than 3 volts to operate and the speaker has a rating of no more than 8 ohms. The sound module may include an integrated circuit, such as an ASIC, for storing data relating to the one or more audible instructions and for causing the speaker to generate the one or more audible instructions. At least part of the sound module may also be a MEMS device. The sound module may be provided within a second housing that includes written instructions for proper use of the respiratory drug delivery apparatus. The second housing may include first and second arms structured to wrap partially around the housing. In another particular embodiment, the respiratory drug delivery apparatus is a valved holding chamber having a chamber housing and a mouthpiece assembly including the mouthpiece attached to an end of the housing, and the second housing includes a first flange portion structured to be received between the mouthpiece assembly and the end of the housing to couple the second housing to the housing. Alternatively, the valved holding chamber may include a chamber housing and an MDI adapter attached to an end of the chamber housing, and the second housing may include a flange portion structured to be received between the MDI adapter and the end of the housing to couple the second housing to the housing. In still another particular embodiment, the respiratory drug delivery apparatus is a valved holding chamber having a chamber housing and a mouthpiece assembly attached to an end of the housing, the mouthpiece assembly includes a mouthpiece and first and second hollow legs, and the second housing includes first and second protruding portions structured to be received within the first and second hollow legs, respectively, to couple the second housing to the housing. The second housing may further include a loop portion opposite the first and second protruding portions structured to wrap around the chamber housing. The second housing may also be structured to snap onto the mouthpiece assembly to couple the second housing to the housing.

In yet another particular embodiment, the apparatus includes an MDI adapter having a hole for receiving an MDI therein, the second housing includes a tab actuating member extending partially over the hole, and the actuation signal is generated in response to the tab actuating member being pushed by the MDI when the MDI is inserted into the hole. Alternatively, the respiratory drug delivery apparatus may be a valved holding chamber having a cap removeably attached to the mouthpiece, wherein the second housing includes a recess structured to receive and hold the cap, and wherein the actuation signal is generated in response to the cap being received within the recess. In still another alternative, the respiratory drug delivery apparatus may be a valved holding chamber having a cap removeably attached to the mouthpiece and a tether strap attaching the cap to the second housing, wherein the actuation signal is generated in response to the cap being removed from the mouthpiece and a portion of the tether strap being disengaged from a portion of the second housing.

The invention also provides a method of encouraging proper use of a respiratory drug delivery apparatus that includes detecting on the respiratory drug delivery apparatus that a predetermined instruction triggering event has occurred, and generating one or more audible instructions relating to proper use of the respiratory drug delivery apparatus from the respiratory drug delivery apparatus in response to the detecting. The method may be implemented in the various apparatus embodiment discussed above.

Therefore, it should now be apparent that the invention substantially achieves all the above aspects and advantages. Additional aspects and advantages of the invention will be set forth in the description that follows, and in part will be obvious from the description, or may be learned by practice of the invention. Moreover, the aspects and advantages of the invention may be realized and obtained by means of the instrumentalities and combinations particularly pointed out in the appended claims.

The accompanying drawings illustrate presently preferred embodiments of the invention, and together with the general description given above and the detailed description given below, serve to explain the principles of the invention. As shown throughout the drawings, like reference numerals designate like or corresponding parts.

FIGS. 28 and 29 show an embodiment of a valved holding chamber having an audio training device coupled thereto wherein the act of inserting an MDI into the valved holding chamber is the manual actuation that triggers the generation of one or more audible instructions;

Figure 42A:
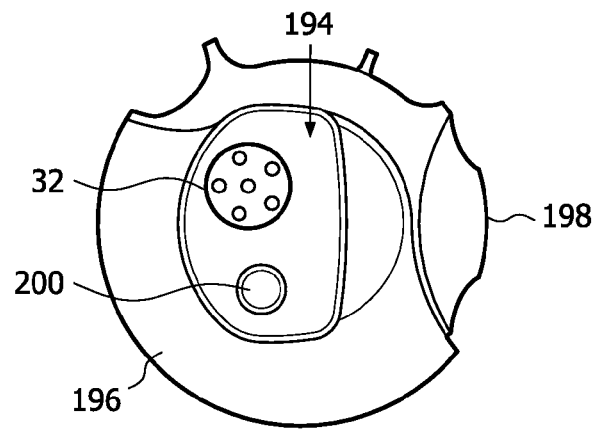
Figure 42B:
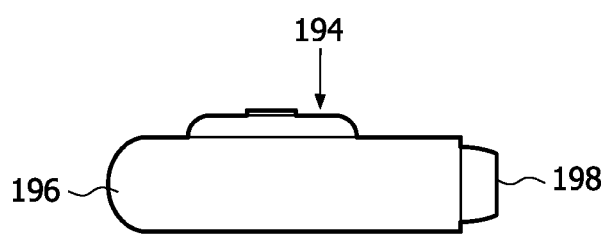
Figure 43:
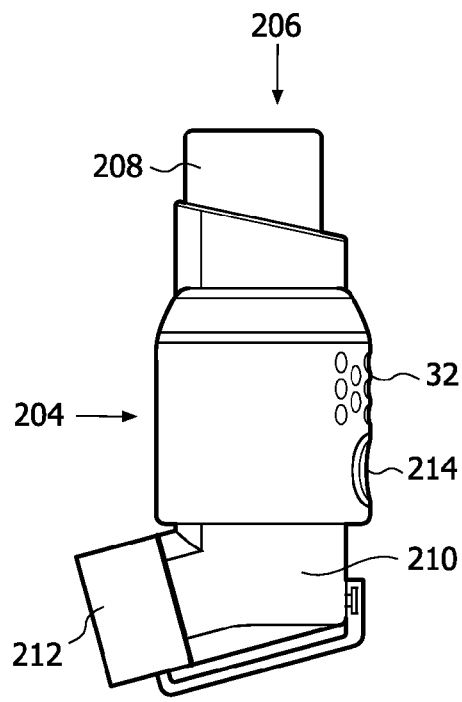

FIGS. 42A, and 42B are top plan and side elevational views of an embodiment of the audio training device coupled to a dry powder inhaler; and FIG. 43 is a side elevational view of an embodiment of the audio training device coupled to a metered dose inhaler (without a holding chamber).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As employed herein, the statement that two or more parts or components are "coupled" together shall mean that the parts are joined or operate together either directly or through one or more intermediate parts or components.

As employed herein, the term "number" shall mean one or an integer greater than one (i.e., a plurality).

The present invention provides various embodiments of an audio training device that may be selectively coupled to a respiratory drug delivery apparatus, such as, without limitation, a valved holding chamber, that generates and provides one or more audible instructions which encourage proper use of the respiratory drug delivery apparatus by the patient.

Figure 1:
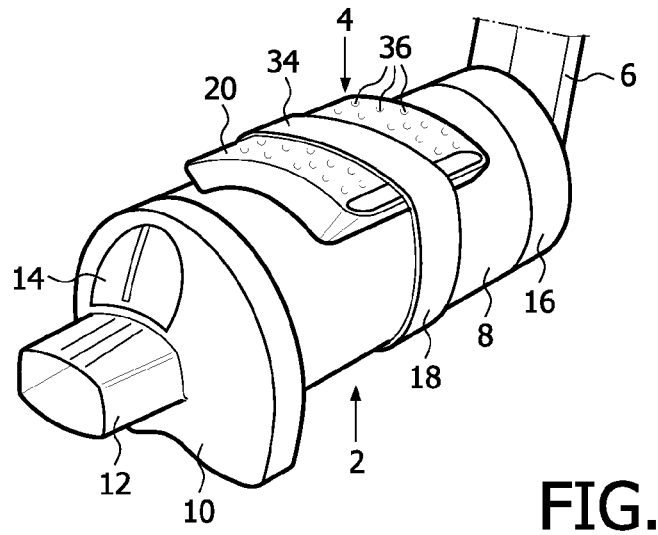
FIGS. 1, 2 and 3 are isometric, side elevational and top plan views, respectively, of a valved holding chamber having an audio training device coupled thereto according to a first embodiment of the present invention.
Figure 2:
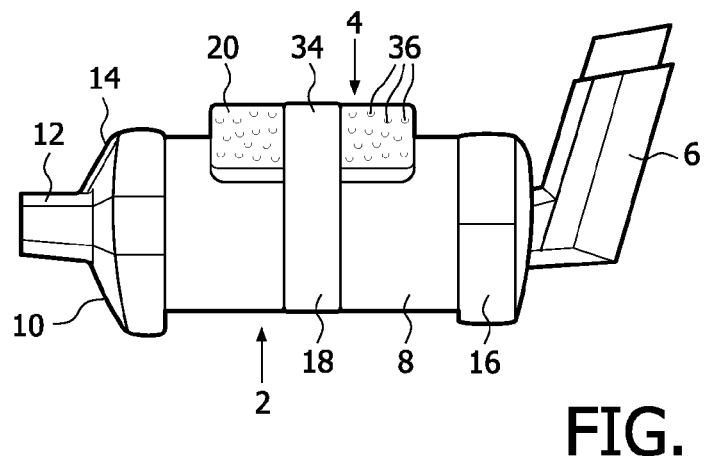
Figure 3:
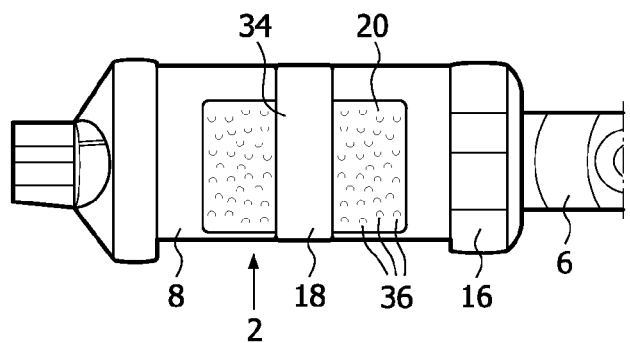

FIGS. 1, 2 and 3 are isometric, side elevational and top plan views, respectively, of a valved holding chamber 2 having an audio training device 4 coupled thereto according to a first embodiment of the present invention. The valved holding chamber 2 is structured to be used in connection with a metered dose inhaler (MDI) 6 as described elsewhere herein. The valved holding chamber 2 includes a generally cylindrical main chamber housing 8 which typically includes a one-way inhalation valve such as an elastomeric valve disk therein. In addition, a mouthpiece assembly 10 is coupled to the front end of the main chamber housing 8 and includes a mouthpiece 12 structured to be received within the lips of the patient during use of the valved holding chamber 2 and an exhalation valve element 14 operatively coupled thereto. The valved holding chamber 2 further includes an MDI adapter 16 which is structured to be removeably attached to the end of the main chamber housing 8 that is opposite the mouthpiece assembly 10. The MDI adapter 16 is structured to receive and hold the MDI 6.

As is known in the art, when the valved holding chamber 2 is used by a patient, the patient inserts the mouthpiece 12 into his or her mouth and exhales in order to at least partially empty gas from the patient's lungs. The exhaled gasses are, through operation of the exhalation valve element 14, allowed to flow from within the mouthpiece assembly 10 to the ambient atmosphere through one or more exhalation ports that are covered by the exhalation valve element 14. Such gasses are not, as a result of the operation of the one-way inhalation valve provided within the main chamber housing 8, permitted to flow into the interior of the main chamber housing 8. Following exhalation, the patient actuates the MDI 6 in order to cause a dose of medication to be sprayed within the main chamber housing 8, and thereafter begins inhaling. During inhalation, the one-way inhalation valve provided within the main chamber housing 8 permits fluid flow from within the main chamber housing 8 into the mouthpiece assembly 10 and out through the mouthpiece 12 so that the medication (mixed with air in the main chamber housing 8) may be deposited within the patient's lungs. This process may be repeated one or more times depending on the needs of the particular patient.

As seen in FIGS. 1, 2 and 3, in that embodiment the audio training device 4 is coupled to the main chamber housing 8 by strap mechanism 18, which may be a single elastic strap sized to fit snugly around the exterior of the main chamber housing 8 or two straps structured to be coupled together beneath the main chamber housing 8 by a suitable fastening mechanism such as, without limitation, Velcro, snaps or an adhesive. The audio training device 4 includes a housing 20, which may be made of a flexible material such as, without limitation, silicone, rubber, a thermoplastic elastomer (TPE), Mylar, plastic, paper or foam, among other materials, or a rigid material. The housing 20 houses therein a sound module 22 which, as described elsewhere herein, is structured to generate one or more audible instructions which encourage proper use of the valved holding chamber 2 by the patient.

Figure 4:
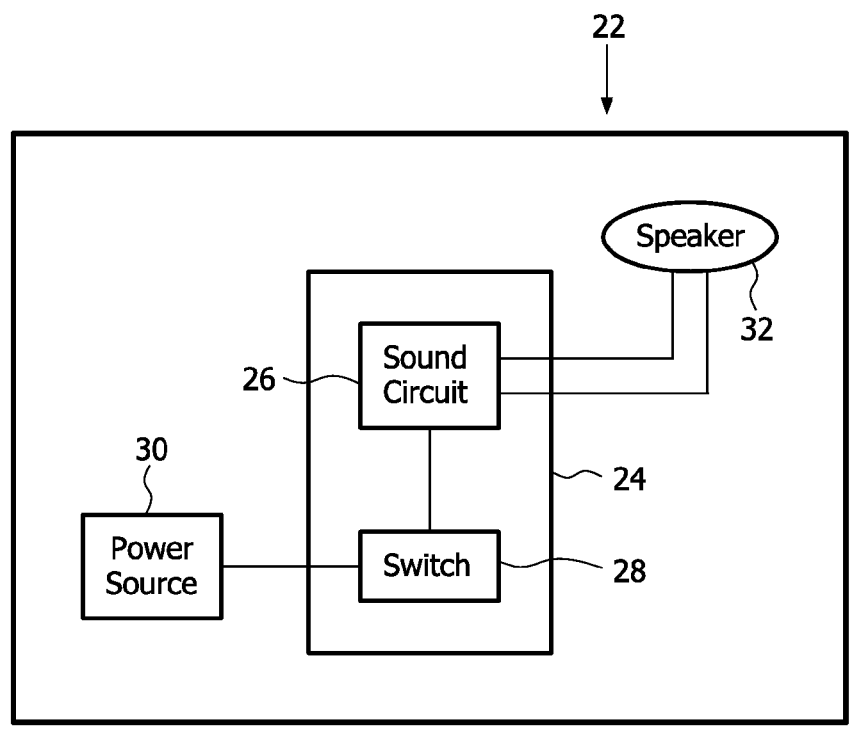
FIG. 4 is a schematic representation of one particular embodiment of a sound module that may be used in the various audio training device embodiments described herein.

FIG. 4 is a schematic representation of one particular embodiment of the sound module 22. The sound module 22 includes a printed circuit board (PCB) 24, which, as is known in the art, may be made of a rigid or flexible material. A sound circuit 26 is mounted on the PCB 24 and includes a controller and a memory that stores audio data including the one or more audible instructions to be provided to the patient according to an aspect of the present invention (which may be prerecorded at the time of manufacture and/or recorded as desired by a patient or a caregiver). For example, the sound circuit 26 may be an application specific integrated circuit (ASIC) that includes a microcontroller or a similar suitable processor and internal memory, such as internal EEPROM and/or Flash memory. As seen in FIG. 4, the sound module 22 also includes a switch 28 provided on the PCB 24 and operatively coupled to the sound circuit 26, a power source 30, such as a battery or a solar cell, operatively coupled to the switch 28 and, through the switch 28, to the sound circuit 26, and a speaker 32 operatively coupled to the sound circuit 26. In response to the actuation of the switch 28, as described in more detail elsewhere herein, the sound circuit 26 is powered by the power source 30 to generate sound (the one or more audible instructions) by using the stored audio data to drive the speaker 32. In the preferred embodiment, the sound module 22 requires no more than 3 volts to operate and the speaker 32 has a rating of no more than 8 ohms. Furthermore, part or all of said sound module 22 may be a MEMS device.

As discussed above, the sound module 22 is housed within the housing 20 of the audio training device 4. In particular, in the embodiment shown in FIGS. 1, 2, and 3, the sound module 22 is positioned within the housing 20 so that the switch 28 is located in a position in which it may be selectively actuated through actuation of a button 34 or a similar manual actuator that is provided on the housing 20. In addition, the housing 20 is preferably provided with a plurality of holes 36 which are positioned over the speaker 32 so that sound may be freely transmitted through the housing 20 by the speaker 32.

In the embodiment shown in FIGS. 1, 2, and 3, the audio training device 4 is preferably adapted to be used as an overall instructional aid which may be employed to provide overall instructions for the proper use of the valved holding chamber 2, especially prior to being used by a patient. In particular, in operation, when the button 34 is actuated by, for example, the patient prior to using the valved holding chamber 2, the switch 28 is actuated which in turns causes the sound circuit 26 to drive the speaker 32 to generate a set of instructions, based on the stored audio data, for the proper use of the valved holding chamber 2. Such instructions may, for example and without limitation, include instructions relating to shaking the MDI 6, actuating the MDI 6, inhaling following the actuation of the MDI 6, and breath holding following the inhalation. Specifically, the set of audible instructions may include, without limitation, an instruction instructing the patient to shake the MDI 6 (either prior to or after inserting it into the valved holding chamber 2), an instruction instructing the patient to actuate the MDI 6 after it has been shaken and inserted into the valved holding chamber 2, an instruction instructing the patient to inhale slowly, for example over predetermined amount of time, and an instruction instructing the patient to hold his or her breath for a predetermined period of time. In another embodiment, the set of audible instructions may include, without limitation, an instruction instructing the patient to shake the MDI 6 (either prior to or after inserting it into the valved holding chamber 2), an instruction instructing the patient to actuate the MDI 6 after it has been shaken and inserted into the valved holding chamber 2, an instruction instructing the patient to take and count a certain number of breaths (e.g., 5 breaths). In still another embodiment, the set of audible instructions may include, without limitation, an instruction instructing the patient to shake the MDI 6 (either prior to or after inserting it into the valved holding chamber 2), an instruction instructing the patient to actuate the MDI 6 after it has been shaken and inserted into the valved holding chamber 2, an instruction instructing the patient to inhale for a particular period of time, such as ten seconds.

Figure 5:
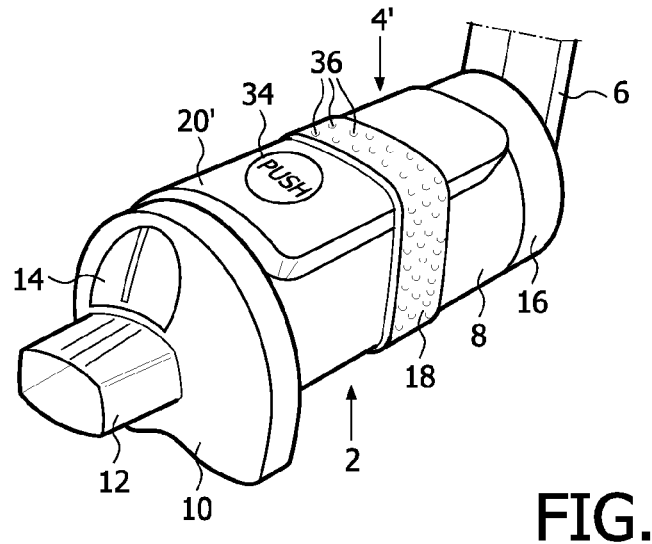
FIGS. 5, 6 and 7 are isometric, side elevational and top plan views, respectively, of a valved holding chamber having an audio training device coupled thereto according to a second embodiment of the present invention.
Figure 6:
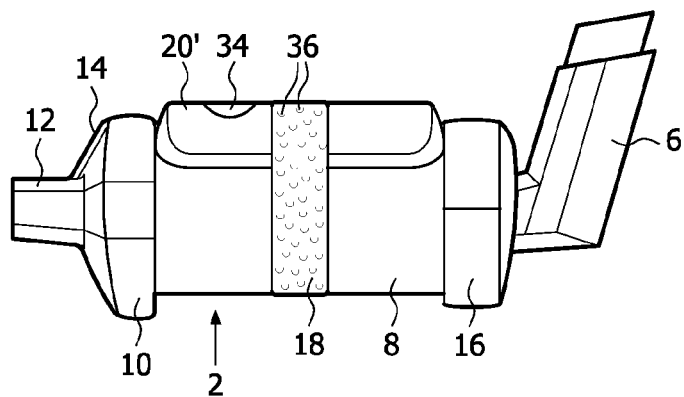
Figure 7:
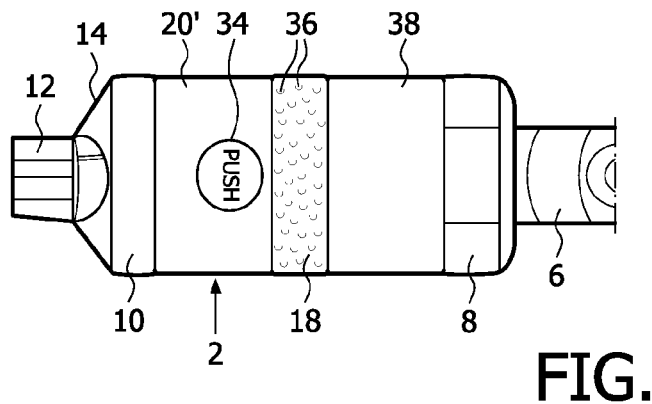

FIGS. 5, 6 and 7 are isometric, side elevational and top plan views, respectively, of a valved holding chamber 2 having an audio training device 4' coupled thereto according to a second embodiment of the present invention. The audio training device 4' is similar to the audio training device 4 except that it includes a housing 20' that is larger than the housing 20. The housing 20' houses a sound circuit 22, which is positioned in a manner such that the switch 28 is located in a position in which it may be selectively actuated through actuation of the button 34 and in a manner in which the plurality of holes 36 are positioned over the speaker 32.

In addition, the top surface of the housing 20' includes a portion 38 on which written instructions for proper use of the valved holding chamber 2 may be provided to supplement the one or more audible instructions that are provided through actuation of the button 34.

Figure 8:
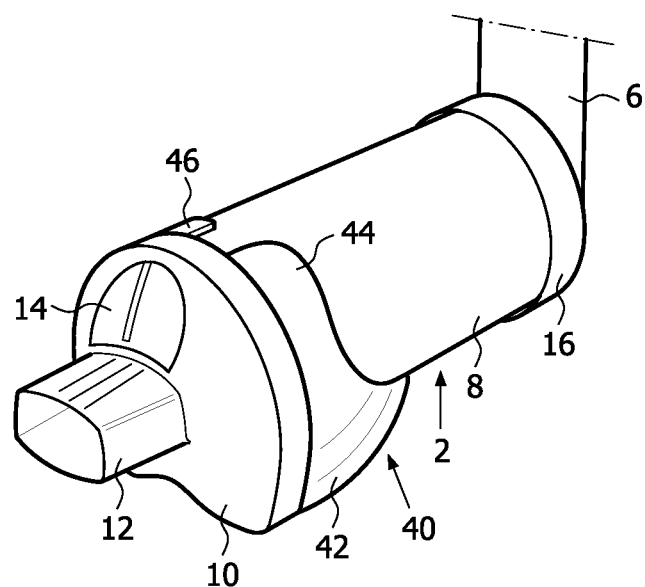
FIGS. 8 and 9 are isometric views and FIGS. 10 and 11 are side elevational and bottom plan views, respectively, of a valved holding chamber having an audio training device coupled thereto according to a third embodiment of the present invention.
Figure 9:
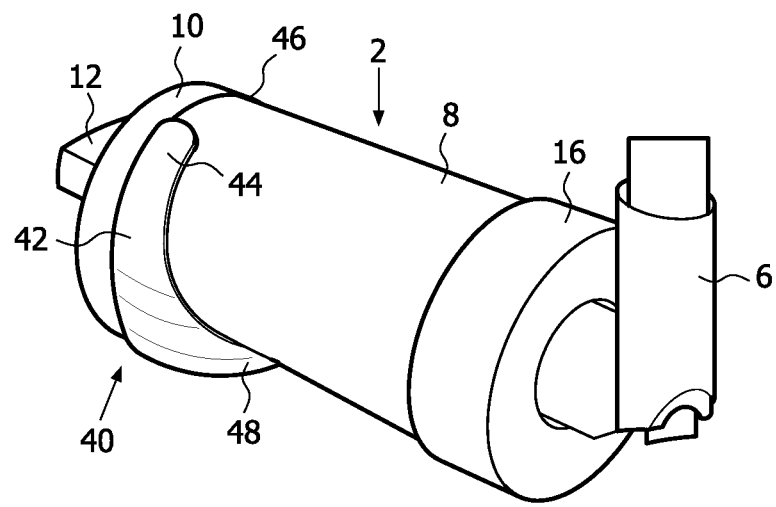
Figure 10:
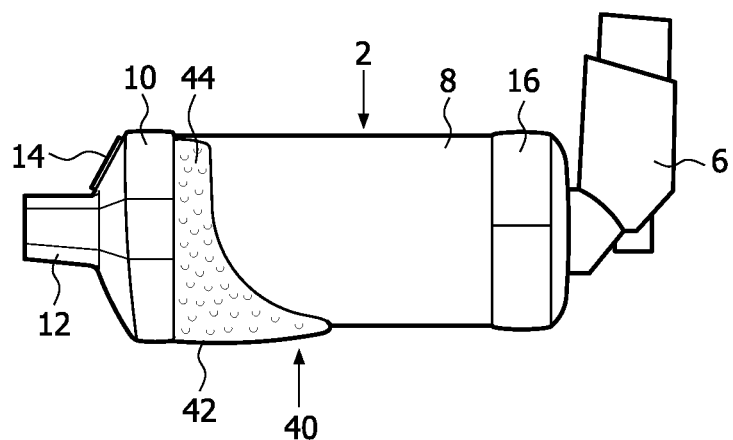
Figure 11:
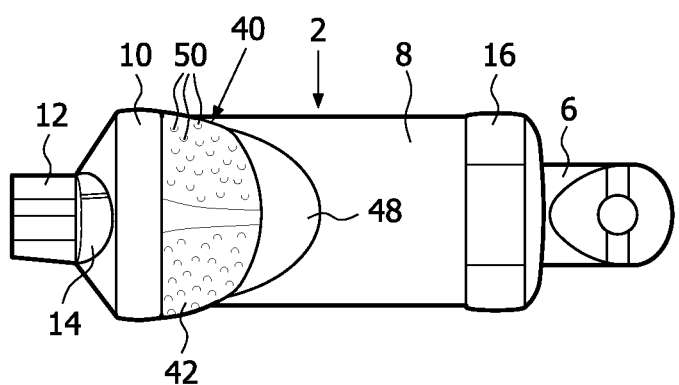

FIGS. 8 and 9 are isometric views and FIGS. 10 and 11 are side elevational and bottom plan views, respectively, of a valved holding chamber 2 having an audio training device 40 coupled thereto according to a third embodiment of the present invention. The audio training device 40 includes a housing 42 having arms 44 and 46 extending therefrom. The housing 42 including the arms 44, 46 have a circular shape when viewed from the front side thereof such that housing 42 including the arms 44, 46 is structured to wrap around the generally cylindrical main chamber housing 8 in order to securely and, preferably removeably, couple the audio training device 40 to the main chamber housing 8. The housing 42 may be made of a rigid material such or a flexible material (as described elsewhere herein) and is sized to generally match the size of the main chamber housing 8 so that it may be slid onto the main chamber housing 8 when either of the mouthpiece assembly 10 or the MDI adapter 16 is separated from the main chamber housing 8. In addition, in an embodiment where the entire housing 42 or just the arms 44 and 46 are made of a resilient flexible material, the audio training device 40 may be coupled to the main chamber housing 8 by pulling the arms 44 and 46 apart and snapping or wrapping them around the main chamber housing, after which they will return to their original shape in order to securely hold the audio training device 40 in place. The housing 42 houses a sound circuit 22, which is positioned in a manner such that the switch 28 is located in a position in which it may be selectively actuated through actuation of the button 48 that is provided at the end of the housing 42 that is opposite the arms 44 and 46 and in a manner in which the plurality of holes 50 are positioned over the speaker 32. In this embodiment, the main portion of the audio training device 40 which houses the sound module 22 is preferably located beneath the main chamber housing 8. Thus, during use, the audio training device 40 will not obscure the patient's and/or the caregiver's view of the exhalation valve element 14.

Figure 12:
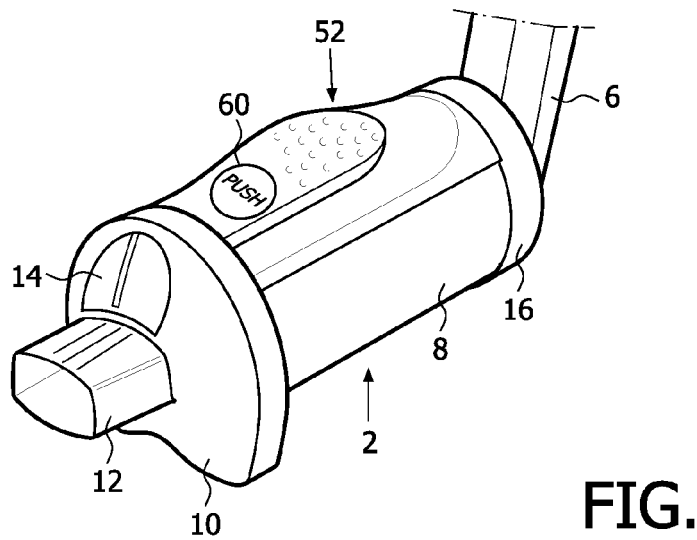
FIGS. 12 and 13 are isometric views of a valved holding chamber having an audio training device coupled thereto according to a fourth embodiment of the present invention.
Figure 13:
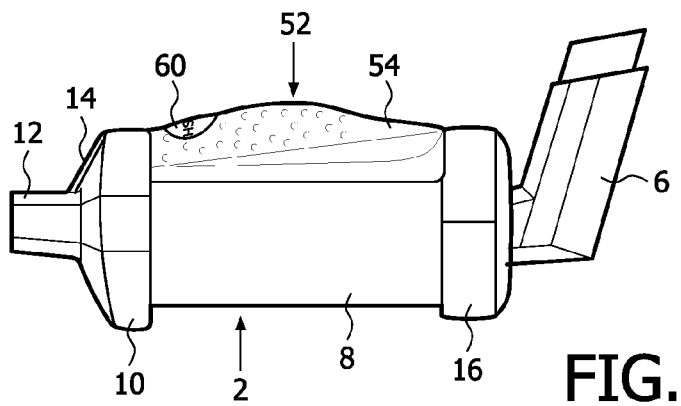
Figure 14:
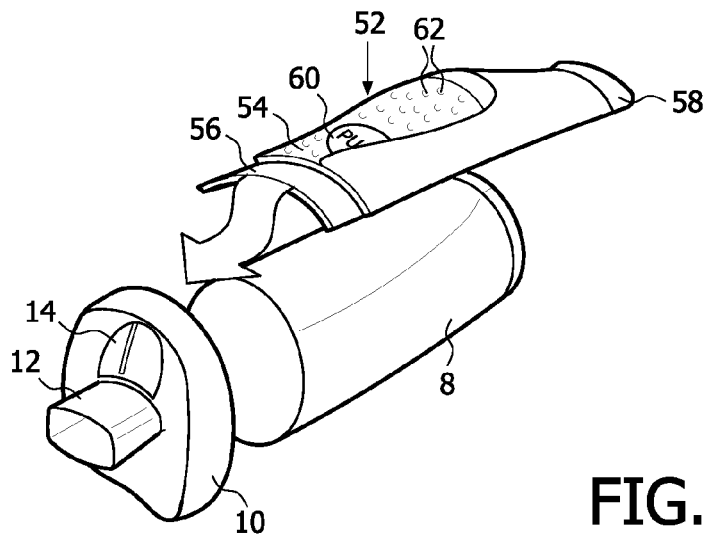
FIG. 14 is a schematic diagram showing the audio training device of FIGS. 12 and 13 and the manner in which it may be coupled to the valved holding chamber.

FIGS. 12 and 13 are isometric views of a valved holding chamber 2 having an audio training device 52 coupled thereto according to a fourth embodiment of the present invention. FIG. 14 is a schematic diagram showing the audio training device 52 and the manner in which it may be coupled to the valved holding chamber 2. As seen in FIG. 14, the audio training device 52 includes a housing 54 having a front flange 56 extending from a first end thereof and a rear flange 58 extending from a second end thereof. The front flange 56 and the rear flange 58 are sized and shaped so that they may be received between the mouthpiece assembly 10 and the main chamber housing 8 and the MDI adapter 16 and the main chamber housing 8, respectively (see FIG. 14), in order to securely and, preferably removeably, couple the audio training device 52 to the valved holding chamber 2. Most preferably, the front and rear flanges 56, 58 comprise a step down from the top surface of the housing 54 so that, when assembled, the top surface of the housing 54 will be flush with the mouthpiece assembly 10 and the MDI adapter 16. The housing 54 may be made of a rigid material such or a flexible material (as described elsewhere herein). The housing 54 houses a sound circuit 22, which is positioned in a manner such that the switch 28 is located in a position in which it may be selectively actuated through actuation of the button 60 that is provided adjacent to the front end of the housing 54 and in a manner in which the plurality of holes 62 are positioned over the speaker 32. In addition, the housing 54 preferably flares outwardly in the manner shown FIGS. 12-14 to provide added room within the housing 54 to accommodate the speaker 32.

Figure 15:
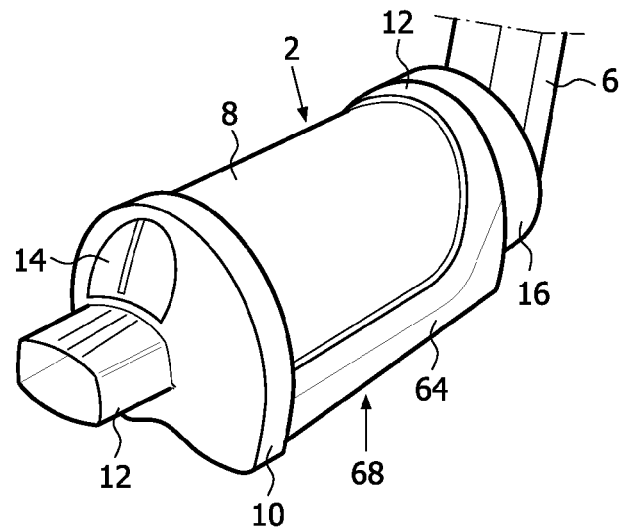
FIGS. 15, 16 and 17 are isometric, side elevational and bottom plan views, respectively, of a valved holding chamber having an audio training device coupled thereto according to a fifth embodiment of the present invention.
Figure 16:
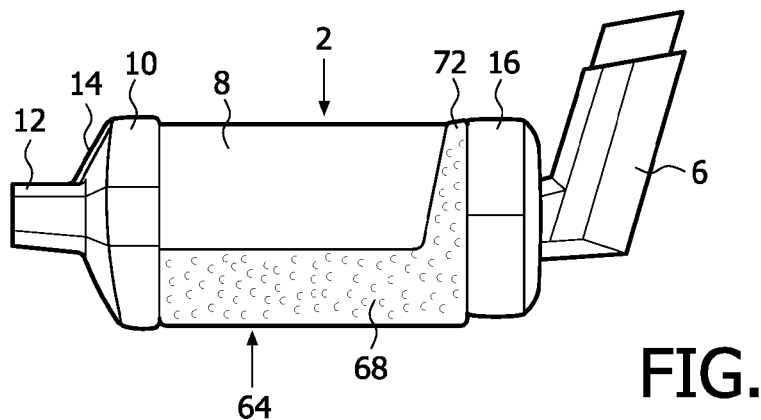
Figure 17:
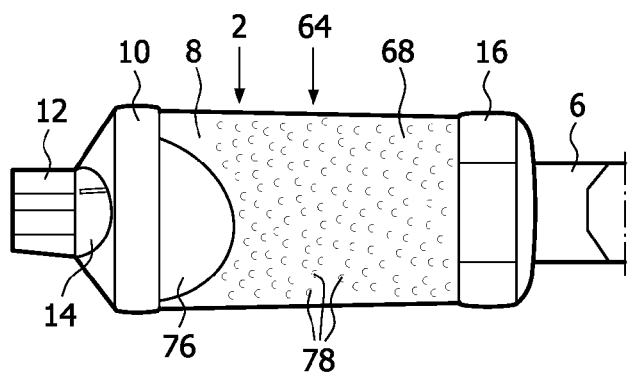
Figure 18:
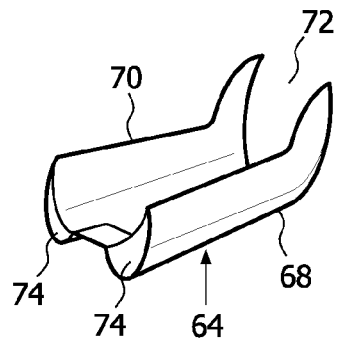
FIG. 18 is an isometric view of the audio training device of FIGS. 15, 16 and 17.
Figure 19:
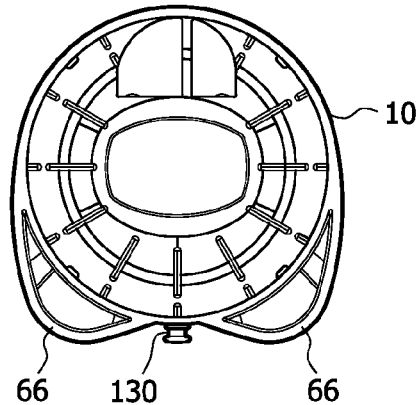
FIG. 19 is a rear elevational view of the main body of the mouthpiece assembly used in that embodiment.

FIGS. 15, 16 and 17 are isometric, side elevational and bottom plan views, respectively, of a valved holding chamber 2 having an audio training device 64 coupled thereto according to a fifth embodiment of the present invention. FIG. 18 is an isometric view of the audio training device 64, and FIG. 19 is a rear elevational view of the main body of the mouthpiece assembly 10 used in this embodiment. As seen in FIG. 19, the embodiment of the mouthpiece assembly 10 shown therein included hollow legs 66, the significance of which is described below. The audio training device 64 includes a housing 68 having a concave top surface 70 and a generally circular loop portion 72 provided at a rear end thereof. In addition, the front end of the housing 68 includes protruding portions 74 which are sized and shaped to be received within and held by the hollow legs 66 of the mouthpiece assembly 10. In order to couple the audio training device 64 to the valved holding chamber 2, the MDI adapter 16 is removed, and the main chamber housing 8 is placed within the concave top surface 70 such that the rear end of the main chamber housing 8 is received within the loop portion 72. In addition, the protruding portions 74 are inserted within the legs 66 of the mouthpiece assembly 10. Thereafter, the MDI adapter is attached to the rear of the main chamber housing 8. As a result, the audio training device 64 is securely, and preferably removeably, coupled to the valved holding chamber 2.

The housing 68 may be made of a rigid material such or a flexible material (as described elsewhere herein). As in the other embodiments, the housing 68 houses a sound circuit 22, which is positioned in a manner such that the switch 28 is located in a position in which it may be selectively actuated through actuation of the button 76 that is provided adjacent to the front end of the housing 68 and in a manner in which the plurality of holes 78 are positioned over the speaker 32.

Figure 20:
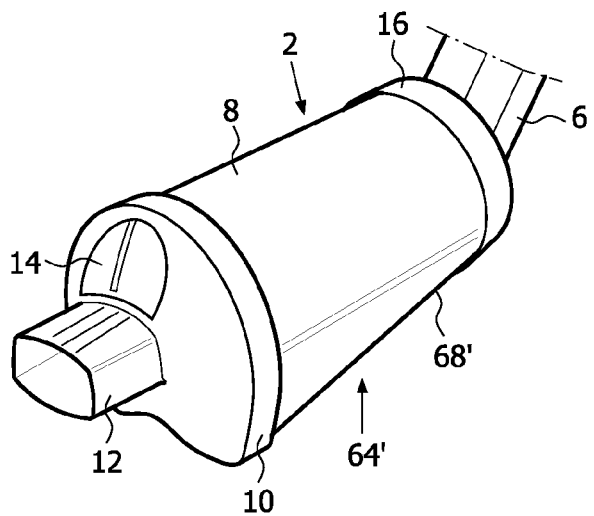
FIGS. 20, 21 and 22 are isometric, side elevational and bottom plan views, respectively, of a valved holding chamber having an audio training device coupled thereto according to a sixth embodiment of the present invention.
Figure 21:
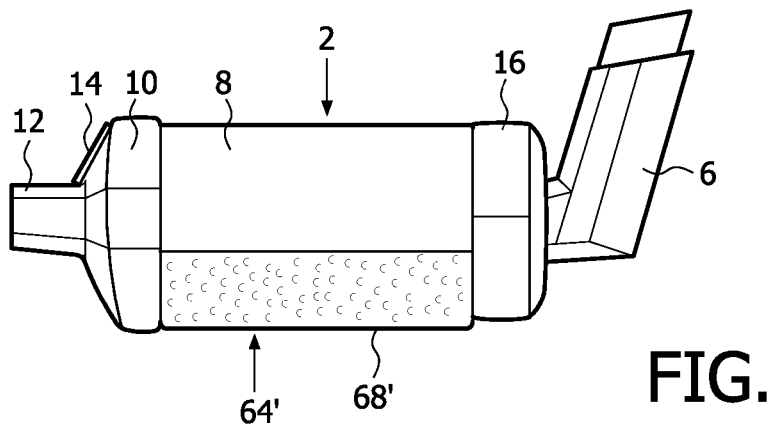
Figure 22:
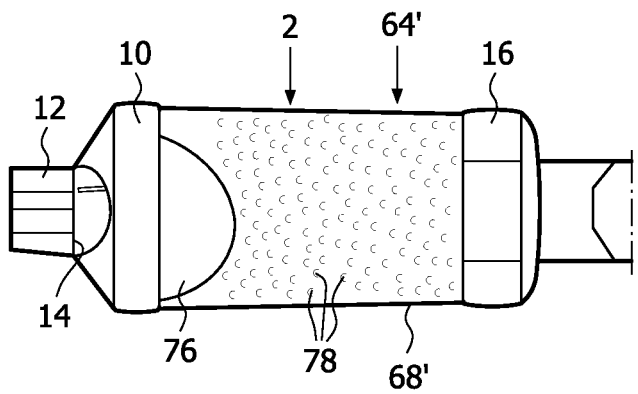
Figure 23:
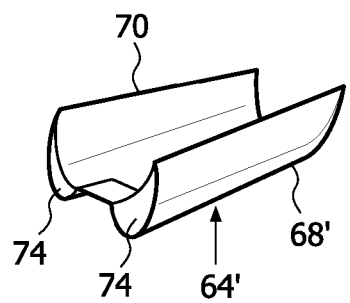
FIG. 23 is an isometric view of the audio training device of FIGS. 20, 21 and 22.

FIGS. 20, 21 and 22 are isometric, side elevational and bottom plan views, respectively, of a valved holding chamber 2 having an audio training device 64' coupled thereto according to a sixth embodiment of the present invention. FIG. 23 is an isometric view of the audio training device 64'. The audio training device 64' is similar to the audio training device 64, except that the audio training device 64' does not include the loop portion 72 that is included in the audio training device 64. The audio training device 64' is thus securely, and preferably removeably, coupled to the valved holding chamber 2 as a result of the protruding portions 74 (extending form the housing 68) being received within the legs 66 of the mouthpiece assembly 10 shown in FIG. 19. In addition, as seen in FIGS. 20 and 21, the audio training device 64' is preferably tapered from front to back to provide a more streamlined shape.

Figure 24:
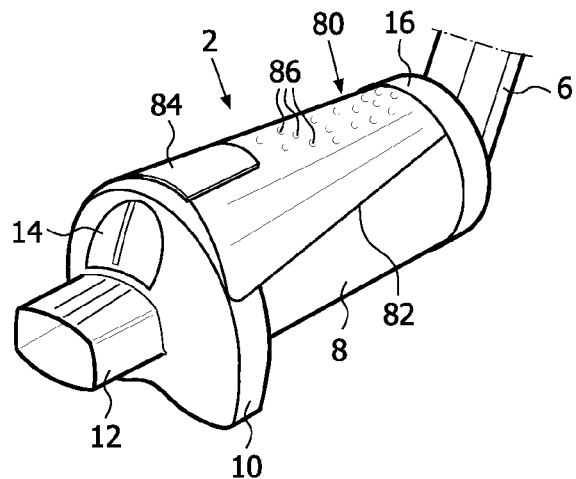
FIG. 24 is an isometric view of a valved holding chamber having an audio training device coupled thereto according to a seventh embodiment of the present invention.

FIG. 24 is an isometric view of a valved holding chamber 2 having an audio training device 80 coupled thereto according to a seventh embodiment of the present invention. The audio training device 80 has a housing 82 that is securely, and preferably removeably, coupled to the valved holding chamber 2 through cooperating snap mechanisms provided on a bottom surface of the front and rear of the housing 82 and correspondingly on the mouthpiece assembly 10 and the MDI adapter 16. In addition, the audio training device 80 is preferably tapered from front to back to provide a more streamlined shape. The housing 82 may be made of a rigid material such or a flexible material (as described elsewhere herein). As in the other embodiments, the housing 82 houses a sound circuit 22, which is positioned in a manner such that the switch 28 is located in a position in which it may be selectively actuated through actuation of the button 84 (e.g., by the patient's forefinger) that is provided adjacent to the front end of the housing 82 and in a manner in which the plurality of holes 86 are positioned over the speaker 32.

Figure 25:
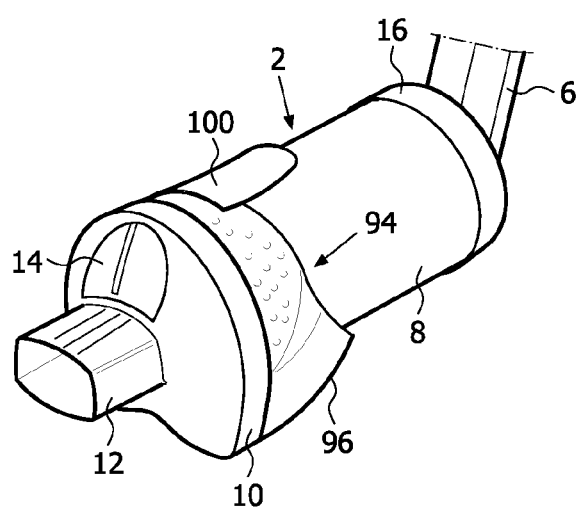
FIGS. 25 and 26 are isometric and side elevational views, respectively, of a valved holding chamber having an audio training device coupled thereto according to an eighth embodiment of the present invention.
Figure 26:
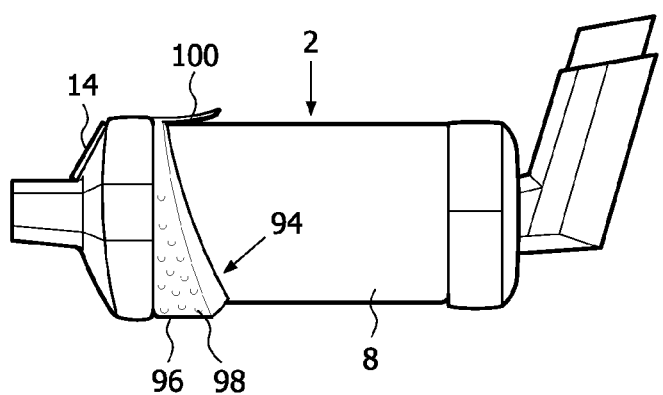

FIGS. 25 and 26 are isometric and side elevational views, respectively, of a valved holding chamber 2 having an audio training device 94 coupled thereto according to an eighth embodiment of the present invention. The audio training device 94 includes a housing 96 having a generally circular shape (in the form of a loop), with a larger, main portion 98 thereof for housing a sound module 22 being located on a bottom side thereof. The housing 96 further includes protruding portions similar to protruding portions 74 (FIGS. 18 and 23) which are sized and shaped to be received within and held by the hollow legs 66 of the mouthpiece assembly 10 employed in this embodiment. In order to couple the audio training device 94 to the valved holding chamber 2, the MDI adapter 16 is removed, and the main chamber housing 8 is inserted through the looped housing 96. In addition, the protruding portions are inserted within the legs 66 of the mouthpiece assembly 10. Thereafter, the MDI adapter 16 is attached to the rear of the main chamber housing 8. As a result, the audio training device 94 is securely, and preferably removeably, coupled to the valved holding chamber 2. The housing 96 may be made of a rigid material such or a flexible material (as described elsewhere herein). As in the other embodiments, the housing 96 houses a sound circuit 22. However, in this embodiment, the switch 28 is located near the top of the housing 96 in a position in which it may be selectively actuated through actuation of the button 100 (e.g., by the patient's forefinger). The speaker 32 is positioned so as to be beneath the plurality of holes provided in the bottom of the housing 96.

Figure 27:
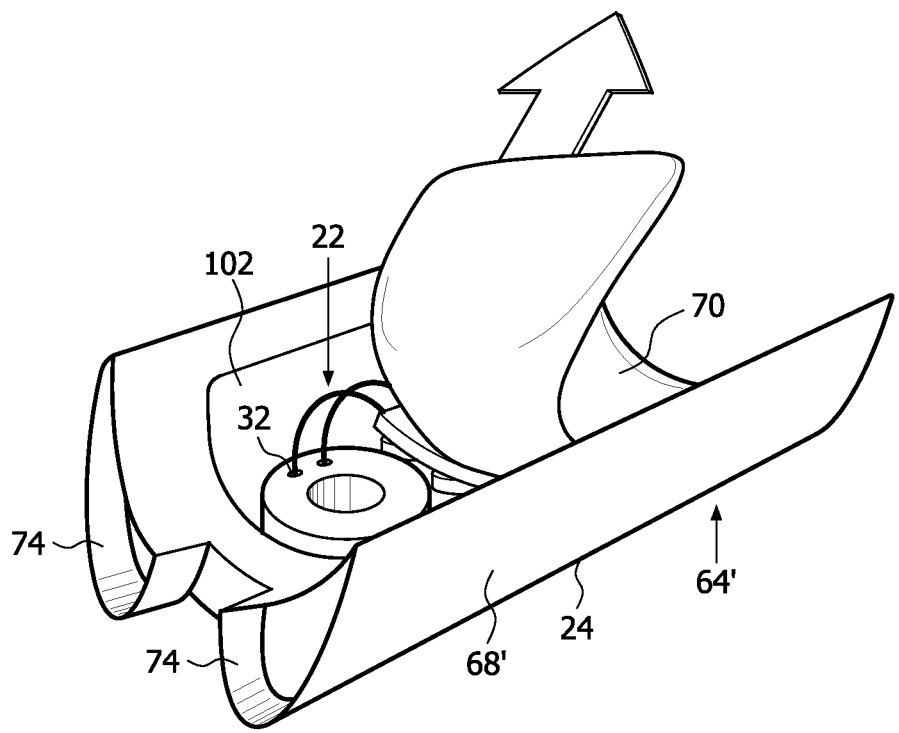
FIG. 27 is a schematic diagram showing how the sound module may be housed within a housing in any of the various embodiment described herein.

FIG. 27 is a schematic diagram showing how the sound module 22 may be housed within a housing in any of the various embodiment described herein. In particular, FIG. 27 is an isometric view of one particular embodiment of the audio training device 64' (FIG. 23). As seen is FIG. 27, in this embodiment, the housing 68' is molded without a top surface and included a cavity 102 in which the sound module 22 is inserted and mounted. Then, a top surface 70, for example in the form of an adhesive backed member, is provided over the cavity and adhered to the remainder of the housing 68' in order to cover and protect the sound module 22. It is to be understood that the audio training device 64' is shown for illustrative purposes (to show how the sound module 22 may be housed within a housing) and that a similar adhesive backed member may be used to cover a similar cavity for housing the sound module 22 provided in the other audio training device embodiments described herein.

In the embodiments descried thus far, the particular manual actuator used to manually actuate the switch 28 has been a button (e.g., 34, 48, 60, 76, 84, and 100). It will be appreciated, however, that a number of alternative manual actuators are also possible. For example, FIGS. 28 and 29 show an embodiment wherein the act of inserting the MDI 6 into the valved holding chamber 2 is the manual actuation that triggers the generation of the one or more audible instructions. In particular, FIGS. 28 and 29 are isometric views of a valved holding chamber 2 having an audio training device 104 coupled thereto according to a ninth embodiment of the present invention. The audio training device 104 includes a housing 106 having a generally circular interior (in the form of a loop), with a larger, main portion 108 thereof for housing a sound module 22. The circular interior of the housing 106 is structured to firmly wrap around the MDI adapter 16 in order to securely couple the audio training device 104 to the valved holding chamber 2. The housing 106 may be made of a rigid material such or a flexible material (as described elsewhere herein). The housing 106 includes a flexible, resilient tab actuating member 110 extending from the main portion 108 which is structured to extend partially over the receiving hole 112 of the MDI adapter 16. The tab actuating member 110 includes a notch 114 which is structured to receive the bottom edge 116 of the outlet 118 of the MDI 6 when it is inserted in the MDI adapter 16. As a result of such action, the tip of the tab actuating member 110 will be pushed downwardly and against the face 120 of the MDI adapter 16. In this embodiment, the switch 28 of the sound module 22 is located near the face 120 of the MDI adapter 16 in a position in which it will be actuated when the tip of the tab actuating member 110 is pushed downwardly and against the face 120 as just described, thereby causing the audible instructions to be generated. The speaker 32 is positioned so as to be beneath the plurality of holes 122 provided in the main portion 108 of the housing 106.

Figure 30:
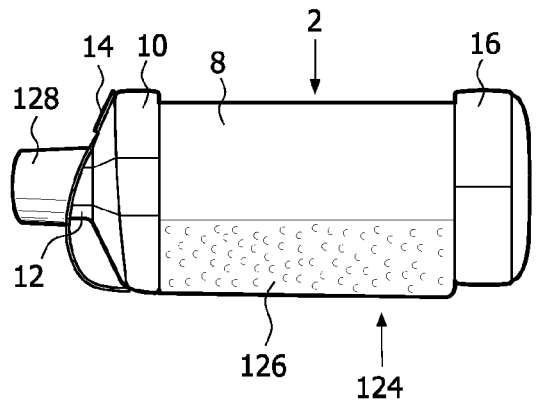
FIGS. 30, 31, 32, 33 and 34 show two embodiments of a valved holding chamber having an audio training device coupled thereto wherein the act of removing a mouthpiece cap and inserting it into a cap holding recess is the manual actuation that triggers the generation of one or more audible instructions.
Figure 31:
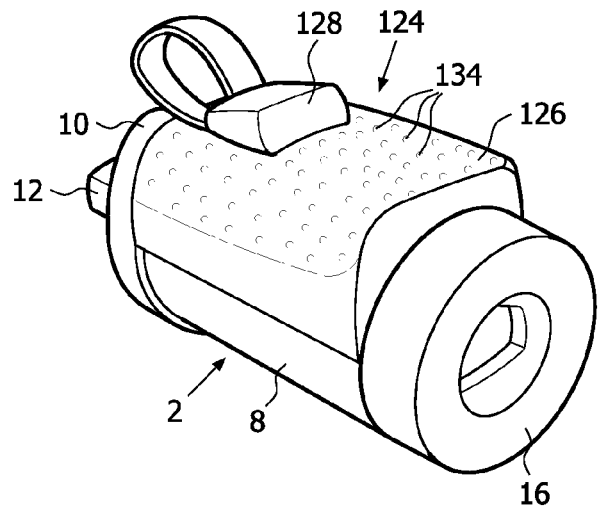
Figure 32:
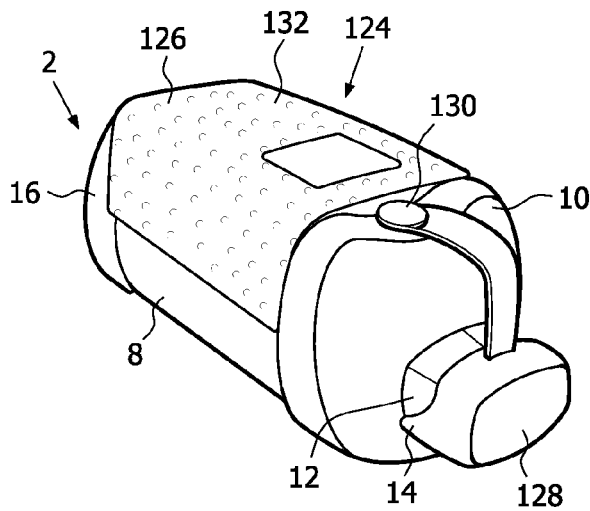
Figure 33:
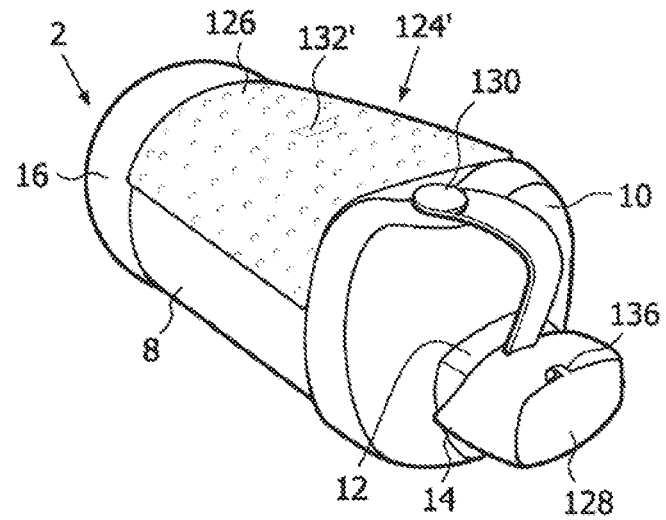
Figure 34:
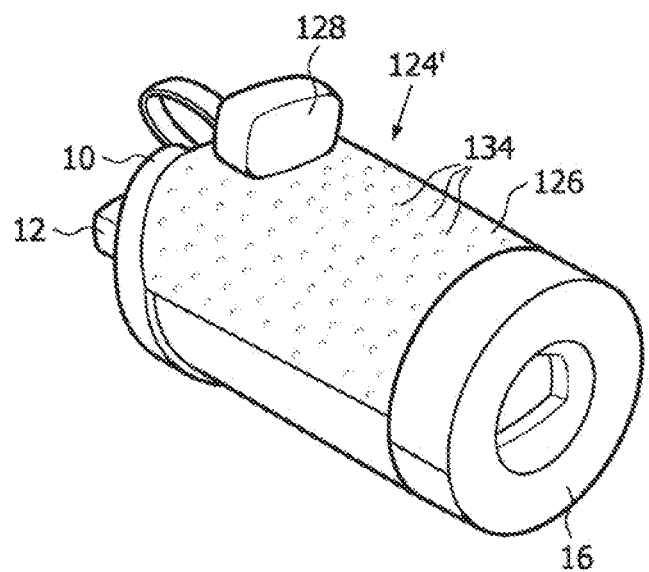

As another example, FIGS. 30, 31 and 32 show an embodiment wherein the act of removing a mouthpiece cap and inserting it into a cap holding recess is the manual actuation that triggers the generation of the one or more audible instructions. In particular, FIG. 30 is a side elevational view and FIGS. 31 and 32 are isometric views of a valved holding chamber 2 having an audio training device 124 coupled thereto according to a tenth embodiment of the present invention. The audio training device 124 includes a housing 126 for housing a sound module 22. The housing 126 may be made of a rigid material such or a flexible material (as described elsewhere herein). Preferably, the housing 126 extends for the entire length of the main chamber housing 8 to provide maximum internal space. The audio training device 124 may, for example, be securely coupled to the valved holding chamber 2 in the manner shown in, for example, FIGS. 12-14, or, alternatively, in any other suitable manner, such as, without limitation, in the manners shown in the other embodiments descried herein. The valved holding chamber 2 includes a tethered cap 128, which covers the mouthpiece 12 and is tethered to a tether peg 130 of the mouthpiece assembly 10. As seen in FIG. 30, the cap 128 preferably has a shape which follows the outer contour of the mouthpiece assembly 10. The housing 126 includes a recess 132 that is structured to receive and hold the cap 128 therein as shown in FIG. 31 (preferably so that the cap will be locked in place by, for example, a secure snap fit). The switch 28 of the sound module 22 is located below the recess 132 in a position in which it will be actuated when the cap 128 is inserted therein as just described, thereby causing the audible instructions to be generated. The speaker 32 is positioned so as to be beneath the plurality of holes 134 provided in the housing 126. FIGS. 33 and 34 show an alternative embodiment of the audio training device 124, designated 124', that includes a smaller recess 132' that is structured to receive and securely hold (e.g., by a secure snap-fit) a finger tab 136 provided on the cap 128. When the finger tab 136 is inserted within the recess 132', the switch 28, positioned below the recess 132', will be actuated and the audible instructions will be generated.

FIGS. 35-38 show various embodiments wherein the act of removing a mouthpiece cap is the manual actuation that triggers the generation of the one or more audible instructions. In these embodiments, however, the removal of the mouthpiece cap causes an electrical connection within the sound module 22 to be broken. The breaking of that electrical connection in turn causes the sound module 22 to generate the one or more audible instructions as described elsewhere herein.

Figure 35:
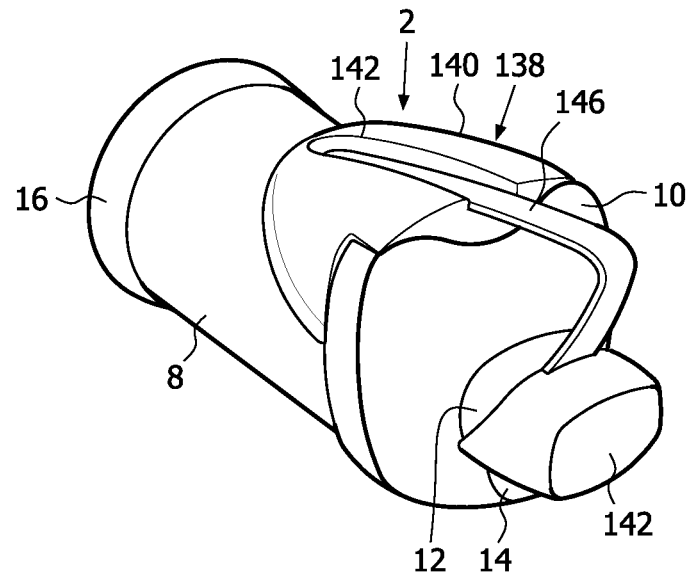
FIGS. 35-38 show various embodiments of a valved holding chamber having an audio training device coupled thereto wherein the act of removing a mouthpiece cap is the manual actuation that triggers the generation of the one or more audible instructions.
Figure 36:
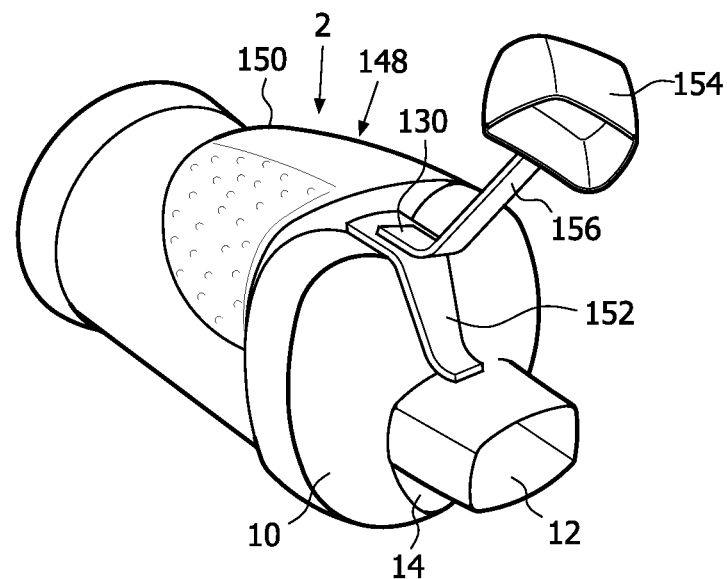
Figure 37:
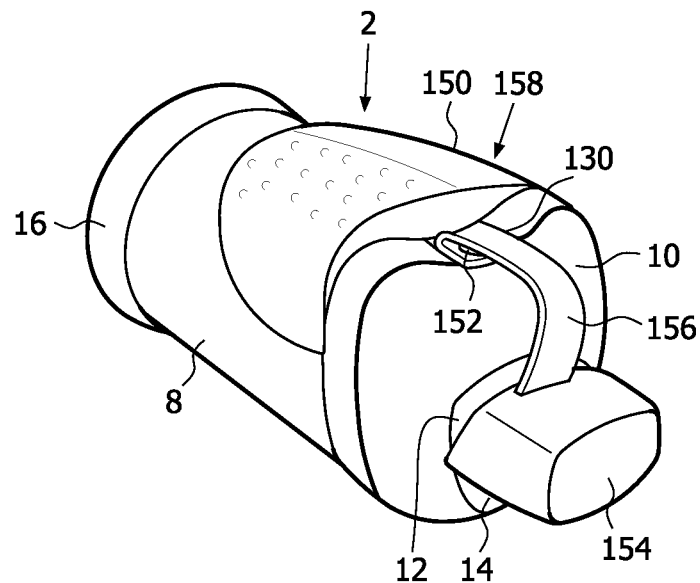
Figure 38:
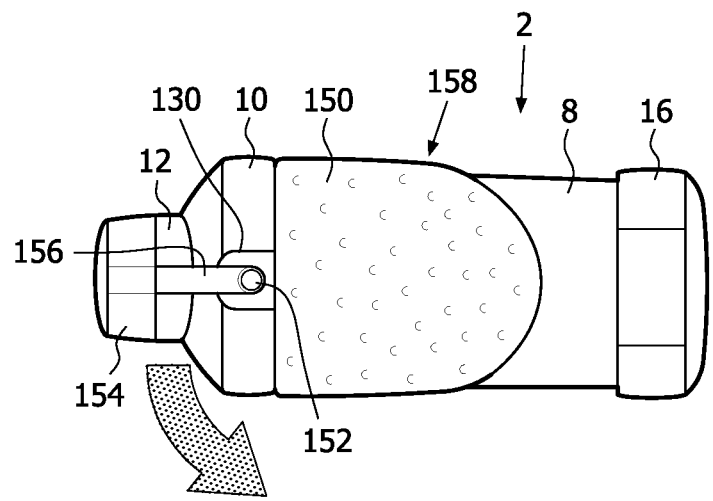

FIG. 35 is an isometric view of a valved holding chamber 2 having an audio training device 138 coupled thereto according to an eleventh embodiment of the present invention. The audio training device 138 includes a housing 140 for housing a sound module 22. The housing 126 may be made of a rigid material such or a flexible material (as described elsewhere herein). The audio training device 138 may, for example, be securely coupled to the valved holding chamber 2 in the manner shown in, for example, FIGS. 20-23, or, alternatively, in any other suitable manner, such as, without limitation, in the manners shown in the other embodiments descried herein. The valved holding chamber 2 includes a tethered cap 142, which covers the mouthpiece 12 and is attached to the housing 140 within a recess 144 by a tether strap 146. When the tether strap 146 is fully seated within the recess 142, it causes a temporary electrical connection within the sound module 22 to be completed. For example, and without limitation, the tether strap 146 may include a conductor that is positioned so as to complete the electrical connection within the sound module 22. Alternatively, the tether strap 146, when fully seated within the recess 142, may apply a pressure within the housing 140 that causes the electrical connection within the sound module 22 to be completed. When the cap 142 is removed from the mouthpiece 12, the tether strap 146 will no longer be fully seated within the recess 142, thereby causing the temporary electrical connection within the sound module 22 to be broken, which triggers the generation of the instructions. FIGS. 36-38 show alternative embodiments wherein the removal of a mouthpiece cap causes an electrical connection within the sound module 22 to be broken, which in turn causes the sound module 22 to generate the one or more audible instructions. Specifically, FIG. 36 is an isometric view of a valved holding chamber 2 having an audio training device 148 coupled thereto according to a twelfth embodiment of the present invention. The audio training device 148 is similar to the audio training device 138, except that instead of having a housing 140 having a recess 142, it has a housing 150 having an arm 152 which extends down the mouthpiece assembly 10 to the mouthpiece 12 as shown in FIG. 36. The arm 152 includes conductors which are used to make the temporary electrical connection as described elsewhere herein when the tether strap 156 of the cap 154 is in contact therewith, either as a result of pressure being applied by the tether strap 156 to close a contact or as a result of a conductor provided as part of the strap 156 that completes the connection as described elsewhere herein. When the cap 152 is removed from the mouthpiece 12, the tether strap 156 will no longer engage the arm, and the electrical connection within the sound module will be broken, thereby triggering the generation of the one or more audible instructions. FIGS. 37 and 38 are isometric and top plan views, respectively, of a valved holding chamber 2 having an audio training device 158 coupled thereto according to a thirteenth embodiment of the present invention. The audio training device 158 is similar to the audio training device 148, except that it has a housing 150 having a shorter arm 152' extending therefrom. In this embodiment, the act of removing the cap 154 and rotating it and the tether strap 156 as shown in FIG. 38 will cause the electrical connection within the sound module housed within the housing 150 to be broken, thereby triggering the generation of the one or more audible instructions.

According to another aspect of the invention, a respiratory drug delivery apparatus is provided wherein particular audio instructions are provided to a patient in response to a particular event or events which occur during use of the respiratory drug delivery apparatus by the patient. For example, in the case of a valved holding chamber, particular audio instructions may be provided in response to the MDI being actuated, the inhalation valve opening or closing (indicating the beginning and end of inhalation, respectively), or a noisemaker such as a whistle emitting a sound. Preferably, as described in more detail below, the particular audio instructions that are provided include one or more instructions relating to a technique for proper use of the respiratory drug delivery apparatus that are specifically related to the particular event that has occurred. The instruction(s) may be a command directed to correcting or preventing a negative behavior relating to use of the respiratory drug delivery apparatus, or, alternatively, a command directed to reinforcing a positive behavior relating to use of the respiratory drug delivery apparatus.

Figure 39:
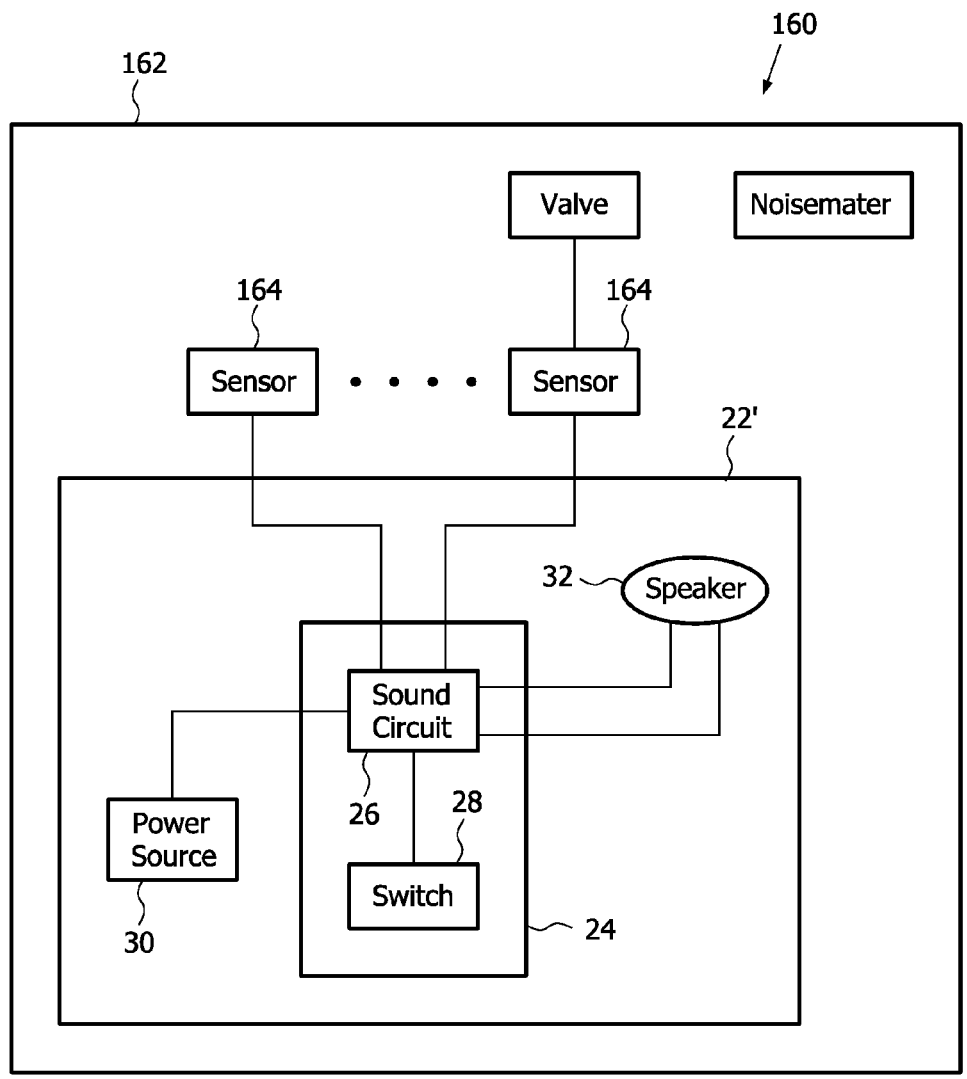
FIG. 39 is a schematic diagram of an embodiment of a respiratory drug delivery apparatus according to an aspect of the invention wherein particular audio instructions are provided to a patient in response to a particular event or events which occur during use of the respiratory drug delivery apparatus by the patient.

FIG. 39 is a schematic diagram of an embodiment of a respiratory drug delivery apparatus 160 according to this aspect of the invention. As seen in FIG. 39, the respiratory drug delivery apparatus 160 includes a housing 162 which houses a modified sound module 22' in which the sound circuit 26 directly receives power from the power source 30. In addition, the housing 162 also houses one or more sensors 164 which are provided for sensing or detecting the occurrence of the events that will trigger the generation of the particular audio instructions described above (for example, as shown in FIG. 39, one or more of the sensors 164 may be operatively coupled to a valve such as an inhalation to sense opening and closing of the valve). In particular, when a sensor 164 senses the occurrence of a predetermined event, the sensor will generate an actuation signal which is sent to the sound circuit 26. In response to the particular actuation signal that is received (i.e., depending on which sensor generated the signal and thus which particular event was detected), the sound circuit 26 will select a data relating to an instruction or set of instructions from its internal memory that corresponds to the actuation signal, and will then drive the speaker 32 to cause it to generate the particular audible instruction or instructions based in the retrieved data. The instruction or set of instructions may relate to proper inhalation technique and/or proper breath hold technique. In the preferred embodiment, the sound module 22' requires no more than 3 volts to operate and the speaker 32 has a rating of no more than 8 ohms.

As mentioned above, the event that is sensed may be the actuation of the MDI by the patient. In such a case, one or more of the sensors 164 may be used to sense the spray of medication within the main chamber housing 8 of a valved holding chamber 2 as shown herein. Those sensors 164 may constitute an optical sensor for optically sensing such a spray of medication, and may include a photo-emitter and a photo-detector for such purposes. Alternatively, one or more of the sensors 164 may be a pressure sensor or a flow sensor for sensing, for example, the spray of medication and/or the beginning and/or end of inhalation by sensing flow levels or open and closed states of an inhalation valve.

In addition, as is known in the art, may respiratory drug delivery apparatus, such as a valved holding chamber, include an airflow actuated noisemaker integrally formed therein (see FIG. 39). The noisemaker may be, for example, a whistle or, alternatively, a device including a sound reed which is caused to vibrate by air flowing thereover. The noisemaker may, for example, be a high airflow indicator that is structured to generate a noise when the air flowing through the respiratory drug delivery apparatus as a result of patient inhalation exceeds some predetermine level, in which case the noisemaker provides a cautionary indication to the patient that the patient is inhaling too quickly and should slow down. One of the sensors 164 may therefore comprise a microphone which will trigger the generation of an instruction instructing the patient to slow his or her breathing down when the noise from the noisemaker is sensed. As will be appreciated, the scenarios just described are merely exemplary, and it will be appreciated that other types of sensors 164 may be employed to detect the occurrence of various events of interest.

Figure 40:
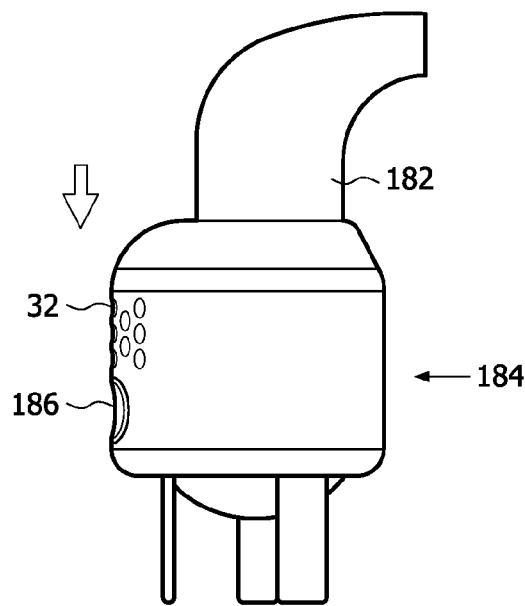
FIGS. 40 and 41 are side elevational views of an embodiment of the audio training device coupled to a jet nebulizer.
Figure 41:
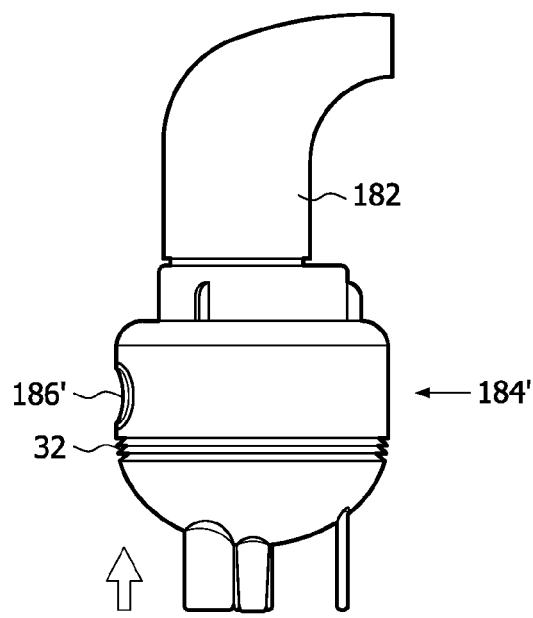

As seen in FIGS. 40, and 41, the audio training device 184, 184' may be coupled to a jet nebulizer 182 rather than a valved holding chamber. FIG. 40 shows the audio training device 184 as a skirt which is slid down over the jet nebulizer 182. FIG. 41 shows the audio training devices 184' as a shell which is slid up onto the jet nebulizer 182. Of course a variety of other structures may be used to couple the audio training device to the jet nebulizer without departing from the scope of the present invention. As in the previous embodiments, these audio trainer devices 184, 184' include a speaker 32 activated by button 186, 186'. Although this embodiment is manually activated through use of button 186, 186', audio training device 184, 184' may alternatively be activated by a sensor, not shown, as described above.

With reference to FIGS. 42A and 42B, an audio trainer 194 may be used with a dry powder inhaler 196. The dry powder inhaler 196 includes a mouthpiece 198 through which the dry powder is inhaled. The audio trainer 194 includes a speaker 32 activated by a button 200. As shown in FIGS. 42A and 42B, the audio trainer 194 may be adhered to the dry powder inhaler 196. Of course, a variety of other structures may be used to couple the audio trainer 194 to the dry powder inhaler 196. Although this embodiment is manually activated through use of button 200, audio training device 194 may alternatively be activated by a sensor, not shown, as described above.

With reference to FIG. 43, an audio trainer 204 may be used with an metered dose inhaler 206. The metered dose inhaler 206 includes a canister 208 fitted within a boot 210. The boot 210 terminates at a mouthpiece 212 through which aerosol is inhaled. The audio trainer 204 includes a speaker 32 activated by a button 214. As shown in FIG. 43, the audio trainer 204 is slid over the boot 210. Of course, a variety of other structures may be used to couple the audio trainer 204 to the boot. Alternatively, the audio trainer may be coupled to the canister 208. Although this embodiment is manually activated through use of button 214, audio training device 204 may alternatively be activated by a sensor, not shown, as described above.

While the various particular embodiments described herein have included a valved holding chamber 2, a jet nebulizer 182, a dry powder inhaler 196, and a metered dose inhaler (without a valved holding chamber), it is to be understood that this is meant to be for illustrative purposes, and that a respiratory drug apparatus of another type may also employ the concepts described herein. As will be appreciated, such devices will typically housing of some type for holding a source of a medication, to which the sound generator describe herein may be coupled, and a patient interface portion, such as a mouthpiece or the like, for delivering one or more doses of the medication to the patient's airway.

While preferred embodiments of the invention have been described and illustrated above, it should be understood that these are exemplary of the invention and are not to be considered as limiting. Additions, deletions, substitutions, and other modifications can be made without departing from the spirit or scope of the present invention. Accordingly, the invention is not to be considered as limited by the foregoing description but is only limited by the scope of the appended claims.

What is claimed is:

1. A respiratory drug delivery apparatus, comprising:
    a housing for holding a source of a medication, said housing having a patient interface portion for delivering one or more doses of said medication to an airway of a patient, wherein the housing includes an inhalation valve configured to enable a patient to inhale through the inhalation valve during delivery of said medication;
    a sound generator coupled to said housing, said sound generator, in response to an actuation signal, being adapted to generate one or more audible instructions, wherein the one or more audible instructions include recorded voice instructions to remedy an improper breathing technique;
    a noisemaker configured to generate a sound in response to airflow caused by inhalation by the patient exceeding a predetermined level;
    a first sensor for sensing an occurrence of an event relating to actuation of said respiratory drug delivery apparatus; and
    a second sensor that includes a microphone, wherein the second sensor is configured to detect the sound generated by the noisemaker, wherein detection by the second sensor indicates that the inhalation by the patient exceeds the predetermined level of airflow;
    wherein said actuation signal is generated in response to an indication of the improper breathing technique for delivery of said medication, wherein the indication is based on the occurrence of the event being sensed by the first sensor and the detection of the sound by the second sensor, wherein the one or more audible instructions instruct the patient to inhale slower, and wherein, when airflow caused by inhalation is below the predetermined level, the noisemaker does not generate a sound.

2. The respiratory drug delivery apparatus according to claim 1, wherein said actuation signal is generated in response to a manual actuation performed by said patient.

3. The respiratory drug delivery apparatus according to claim 2, wherein said sound generator is operatively coupled to a manual actuator, and wherein said manual actuation comprises a manual actuation of said manual actuator.

4. The respiratory drug delivery apparatus according to claim 3, wherein said manual actuator is a button, and wherein said manual actuation comprises a press of said button.

5. The respiratory drug delivery apparatus according to claim 2, further comprising a cap structured to be removeably attached to a portion of said housing, wherein said manual actuation comprises a removal of said cap from said housing.

6. The respiratory drug delivery apparatus according to claim 5, further comprising means for detecting that said cap has been removed from said housing and in response thereto causing said actuation signal to be generated.

7. The respiratory drug delivery apparatus according to claim 2, wherein said manual actuation comprises causing said source of a medication to be held by said housing.

8. The respiratory drug delivery apparatus according to claim 7, wherein said source of a medication is adapted to be inserted at least partially within said housing, and wherein said causing said source of a medication to be held by said housing comprises inserting said source of medication at least partially within said housing.

9. The respiratory drug delivery apparatus according to claim 7, further comprising means for detecting that said source of a medication has been caused to be held by said housing and in response thereto causing said actuation signal to be generated.

10. The respiratory drug delivery apparatus according to claim 2, wherein said one or more audible instructions comprises a set of audible instructions for proper use of said respiratory drug delivery apparatus.

11. The respiratory drug delivery apparatus according to claim 10, wherein said respiratory drug delivery apparatus is an MDI, wherein said housing comprises a canister holder, wherein said patient interface portion is an outlet of said canister holder, wherein said source of a medication is a canister holding said medication, and wherein said set of audible instructions include instructions relating to shaking the MDI, actuating the MDI, inhaling, and breath holding.

12. The respiratory drug delivery apparatus according to claim 11, wherein said set of audible instructions include an instruction instructing the patient to shake the MDI, an instruction instructing the patient to actuate the MDI, an instruction instructing the patient to inhale slowly, and an instruction instructing the patient to hold his or her breath for a predetermined period of time.

13. The respiratory drug delivery apparatus according to claim 10, wherein said respiratory drug delivery apparatus comprises a valved holding chamber, wherein said patient interface portion is a mouthpiece, wherein said source of a medication is an MDI, and wherein said set of audible instructions include instructions relating to shaking the MDI, actuating the MDI, inhaling, and breath holding.

14. The respiratory drug delivery apparatus according to claim 13, wherein said set of audible instructions include an instruction instructing the patient to shake the MDI, an instruction instructing the patient to actuate the MDI, an instruction instructing the patient to inhale slowly, and an instruction instructing the patient to hold his or her breath for a predetermined period of time.

15. The respiratory drug delivery apparatus according to claim 13, wherein said housing includes a chamber housing, an end cap attached to a first end of said chamber housing for receiving and holding said MDI, and a mouthpiece assembly including said mouthpiece attached to a second end of said chamber housing opposite said first end.

16. The respiratory drug delivery apparatus according to claim 10, wherein said respiratory drug delivery apparatus comprises a valved holding chamber, wherein said patient interface portion is a mouthpiece, wherein said source of a medication is an MDI, and wherein said set of audible instructions include instructions relating to shaking the MDI, actuating the MDI, and taking and counting a certain number of breaths.

17. The respiratory drug delivery apparatus according to claim 10, wherein said respiratory drug delivery apparatus comprises a valved holding chamber, wherein said patient interface portion is a mouthpiece, wherein said source of a medication is an MDI, and wherein said set of audible instructions include instructions relating to shaking the MDI, actuating the MDI, and inhaling for a particular period of time.

18. The respiratory drug delivery apparatus according to claim 1, wherein the recorded voice instructions include a command directed to correcting or preventing the improper breathing technique in addition to the instruction to inhale slower.

19. The respiratory drug delivery apparatus according to claim 1, wherein the recorded voice instructions include a command directed to reinforcing a positive behavior relating to use of said respiratory drug delivery apparatus.

20. The respiratory drug delivery apparatus according to claim 1, wherein said respiratory drug delivery apparatus comprises a valved holding chamber, wherein said patient interface portion is a mouthpiece, and wherein said source of a medication is an MDI.

21. The respiratory drug delivery apparatus according to claim 20, wherein said first sensor senses a spray of medication resulting from the actuation of said MDI.

22. The respiratory drug delivery apparatus according to claim 21, wherein said first sensor comprises an optical sensor for optically sensing a presence of said spray within said housing.

23. The respiratory drug delivery apparatus according to claim 1, wherein the one or more audible instructions include instructions related to proper inhalation technique in addition to the instructions to inhale slower.

24. The respiratory drug delivery apparatus according to claim 1, wherein the one or more audible instructions include instructions related to proper breath hold technique.

25. The respiratory drug delivery apparatus according to claim 1, wherein said sound generator is removeably attachable to said housing.

26. The respiratory drug delivery apparatus according to claim 25, wherein said sound generator is provided within a second housing that is removeably attachable to said housing.

27. The respiratory drug delivery apparatus according to claim 26, wherein said second housing is made of a flexible material.

28. The respiratory drug delivery apparatus according to claim 26, wherein said second housing is made of a rigid material.

29. The respiratory drug delivery apparatus according to claim 26, wherein said second housing includes means for removeably attaching said second housing to said housing.

30. The respiratory drug delivery apparatus according to claim 26, wherein said second housing includes written instructions for proper use of said respiratory drug delivery apparatus.

31. The respiratory drug delivery apparatus according to claim 26, wherein said second housing includes first and second arms structured to wrap partially around said housing.

32. The respiratory drug delivery apparatus according to claim 26, wherein said respiratory drug delivery apparatus is a valved holding chamber, wherein said housing includes a chamber housing and a mouthpiece assembly including said mouthpiece attached to an end of said housing, and wherein said second housing includes a first flange portion structured to be received between said mouthpiece assembly and said end of said housing to couple said second housing to said housing.

33. The respiratory drug delivery apparatus according to claim 26, wherein said respiratory drug delivery apparatus is a valved holding chamber, wherein said housing includes a chamber housing and an MDI adapter attached to an end of said chamber housing, and wherein said second housing includes a flange portion structured to be received between said MDI adapter and said end of said housing to couple said second housing to said housing.

34. The respiratory drug delivery apparatus according to claim 26, wherein said respiratory drug delivery apparatus is a valved holding chamber, wherein said housing includes a chamber housing and a mouthpiece assembly attached to an end of said housing, said mouthpiece assembly including said mouthpiece and first and second hollow legs, and wherein said second housing includes first and second protruding portions structured to be received within said first and second hollow legs, respectively, to couple said second housing to said housing.

35. The respiratory drug delivery apparatus according to claim 34, wherein said second housing further includes a loop portion opposite said first and second protruding portions, said loop portion being structured to wrap around said chamber housing.

36. The respiratory drug delivery apparatus according to claim 26, wherein said respiratory drug delivery apparatus is a valved holding chamber, wherein said housing includes a chamber housing and a mouthpiece assembly including said mouthpiece attached to an end of said housing, and wherein said second housing is structured to snap onto said mouthpiece assembly to couple said second housing to said housing.

37. The respiratory drug delivery apparatus according to claim 26, wherein said respiratory drug delivery apparatus is a valved holding chamber, wherein said housing includes a chamber housing and a mouthpiece assembly including said mouthpiece attached to an end of said housing, and wherein said second housing includes a loop portion structured to wrap around said chamber housing to coupled said second housing to said housing.

38. The respiratory drug delivery apparatus according to claim 26, wherein said respiratory drug delivery apparatus is a valved holding chamber, wherein said housing includes a chamber housing and an MDI adapter having a hole for receiving an MDI therein, and wherein said second housing includes a tab actuating member extending partially over said hole, wherein said actuation signal is generated in response to said tab actuating member being pushed by said MDI when said MDI is inserted into said hole.

39. The respiratory drug delivery apparatus according to claim 26, wherein said respiratory drug delivery apparatus is a valved holding chamber having a cap removeably attached to said mouthpiece, wherein said second housing includes a recess structured to receive and hold said cap, and wherein said actuation signal is generated in response to said cap being received within said recess.

40. The respiratory drug delivery apparatus according to claim 26, wherein said respiratory drug delivery apparatus is a valved holding chamber having a cap removeably attached to said mouthpiece and a tether strap attaching said cap to said second housing, wherein said actuation signal is generated in response to said cap being removed from said mouthpiece and a portion of said tether strap being disengaged from a portion of said second housing.

41. The respiratory drug delivery apparatus according to claim 1, wherein said sound generator comprises a sound module having a power source and a speaker, and wherein said sound module requires no more than 3 volts to operate and said speaker has a rating of no more than 8 ohms.

42. The respiratory drug delivery apparatus according to claim 41, wherein said sound module includes an integrated circuit for storing data relating to said one or more audible instructions and for causing said speaker to generate said one or more audible instructions.

43. The respiratory drug delivery apparatus according to claim 42, wherein said integrated circuit is an ASIC.

44. The respiratory drug delivery apparatus according to claim 1, wherein at least part of the sound generator is a MEMS device.

45. A method of encouraging proper use of a respiratory drug delivery apparatus that includes an inhalation valve and a noisemaker, wherein a patient inhales through the inhalation valve during delivery of medication, comprising:
sensing, by a first sensor, an occurrence of an event relating to actuation of the respiratory drug delivery apparatus;
generating a sound, by the noisemaker, in response to airflow caused by inhalation by the patient exceeding a predetermined level;
determining, by a second sensor that includes a microphone, that the predetermined level of airflow is exceeded based upon the sound generated by the noisemaker;
generating an actuation signal in response to an indication of improper breathing technique for delivery of the medication, wherein the indication is based on the occurrence of the event relating to actuation of the respiratory drug delivery apparatus and the determination by the second sensor;
detecting on said respiratory drug delivery apparatus that a predetermined instruction triggering event has occurred, wherein the predetermined instruction triggering event is indicated by the actuation signal; and
generating one or more audible instructions, wherein the one or more audible instructions include recorded voice instructions, wherein the one or more audible instructions instruct the patient to inhale slower, and wherein, when airflow caused by inhalation is below the predetermined level, the noisemaker does not generate a sound.

46. The method according to claim 45, wherein said predetermined instruction triggering event comprises a manual actuation performed by a patient using said respiratory drug delivery apparatus.

47. The method according to claim 46, wherein said manual actuation comprises an actuation of a manual actuator associated with said respiratory drug delivery apparatus.

48. The method according to claim 47, wherein manual actuator is a button provided on said respiratory drug delivery apparatus.

49. The method according to claim 46, wherein said respiratory drug delivery apparatus includes a cap, wherein said manual actuation comprises removal of said cap by a patient using said respiratory drug delivery apparatus.

50. The method according to claim 46, wherein said manual actuation comprises causing a source of medication to be held by said respiratory drug delivery apparatus.

51. The method according to claim 50, wherein said respiratory drug delivery apparatus comprises a valved holding chamber, wherein said source of medication comprises an MDI, and wherein said causing comprises inserting said MDI at least partially within said valved holding chamber.

52. The method according to claim 46, wherein said respiratory drug delivery apparatus comprises an MDI, and wherein said one or more audible instructions comprises a set of audible instructions for proper use of said respiratory drug delivery apparatus including instructions relating to shaking the MDI, actuating the MDI, inhaling, and breath holding.

53. The method according to claim 52, wherein said set of audible instructions include an instruction instructing the patient to shake the MDI, an instruction instructing the patient to actuate the MDI, an instruction instructing the patient to inhale slowly, and an instruction instructing the patient to hold his or her breath for a predetermined period of time.

54. The method according to claim 52, wherein said respiratory drug delivery apparatus further comprises a valved holding chamber for holding said MDI.

55. The method according to claim 46, wherein said respiratory drug delivery apparatus comprises an MDI, and wherein said one or more audible instructions comprises a set of audible instructions for proper use of said respiratory drug delivery apparatus including instructions relating to shaking the MDI, actuating the MDI, and taking and counting a certain number of breaths.

56. The method according to claim 46, wherein said respiratory drug delivery apparatus comprises an MDI, and wherein said one or more audible instructions comprises a set of audible instructions for proper use of said respiratory drug delivery apparatus including instructions relating to shaking the MDI, actuating the MDI, and inhaling for a particular period of time.

57. The method according to claim 45, wherein the recorded voice instructions include a command directed to correcting or preventing the improper breathing technique in addition to the instructions to inhale slower.

58. The method according to claim 45, wherein the recorded voice instructions include a command directed to reinforcing a positive behavior relating to use of said respiratory drug delivery apparatus.

59. The method according to claim 45, wherein said respiratory drug delivery apparatus comprises an MDI.

60. The method according to claim 59, wherein sensing the occurrence of the event relating to actuation comprises sensing a spray of medication resulting from the actuation of said MDI.

61. The method according to claim 45, wherein the one or more audible instructions include instructions related to proper inhalation technique in addition to the instructions to inhale slower.

62. The method according to claim 45, wherein the one or more audible instructions include instructions related to proper breath hold technique.

63. The method according to claim 45, wherein said generating of the one or more audible instructions requires no more than 3 volts and wherein said generating employs a speaker having a rating of no more than 8 ohms.

* * * * *